US011058759B2

(12) United States Patent
Pushko et al.

(10) Patent No.: US 11,058,759 B2
(45) Date of Patent: Jul. 13, 2021

(54) VACCINES AGAINST INFECTIOUS DISEASES CAUSED BY POSITIVE STRANDED RNA VIRUSES

(71) Applicant: Medigen, Inc., Frederick, MD (US)

(72) Inventors: Peter Pushko, Frederick, MD (US); Irina Tretyakova, Frederick, MD (US)

(73) Assignee: Medigen, Inc., Frederick, MD (US)

( * ) Notice: Subject to any disclaimer, the term of this patent is extended or adjusted under 35 U.S.C. 154(b) by 0 days.

(21) Appl. No.: 16/462,383

(22) PCT Filed: Nov. 21, 2017

(86) PCT No.: PCT/US2017/062733
§ 371 (c)(1),
(2) Date: May 20, 2019

(87) PCT Pub. No.: WO2018/098133
PCT Pub. Date: May 31, 2018

(65) Prior Publication Data
US 2019/0314482 A1 Oct. 17, 2019

Related U.S. Application Data

(60) Provisional application No. 62/426,708, filed on Nov. 28, 2016.

(51) Int. Cl.
*A61K 39/12* (2006.01)
*C12N 7/00* (2006.01)
*C12N 15/86* (2006.01)
*A61K 39/00* (2006.01)

(52) U.S. Cl.
CPC ................ *A61K 39/12* (2013.01); *C12N 7/00* (2013.01); *C12N 15/86* (2013.01); *A61K 2039/5254* (2013.01); *A61K 2039/53* (2013.01); *A61K 2039/552* (2013.01); *A61K 2039/70* (2013.01); *C12N 2770/24121* (2013.01); *C12N 2770/24134* (2013.01); *C12N 2770/24143* (2013.01); *C12N 2770/24144* (2013.01); *C12N 2770/24151* (2013.01)

(58) Field of Classification Search
None
See application file for complete search history.

(56) References Cited

U.S. PATENT DOCUMENTS

| | | |
|---|---|---|
| 9,463,233 B2 | 10/2016 | Kinney et al. |
| 2007/0128711 A1 | 6/2007 | Yamshchikov |

OTHER PUBLICATIONS

Johansen et al., PNAS USA, 1996, 93(22):12400-12405. (Year: 1996).*
Tepfer et al., Environ. Biosafety Res., 2004, 3:91-97. (Year: 2004).*
Lutze, et al., "A quick and efficient method for the recovery of plasmid or viral DNA from mammalian cells", Oct. 1990. Nucleic Acids Res, 18(20): 6150-6150.
Nickols, et al., "Plasmid DNA launches live-attenuated Japanese encephalitis virus and elicits virus-neutralizing antibodies in BALB/c mice", Sep. 2017. Virology, vol. 512, pp. 66-73.
International Search Report and Written Opinion dated Feb. 6, 2018 for PCT application No. PCT/US2017/062733, 15 pages.
Tretyakova et al., "Plasmid DNA initiates replication of yellow fever vaccine in vitro and elicits virus-specific immune response in mice," 2014. Virology, 468-470. pp. 28-35.
Yamshchikov, et al., "A New Strategy in Design of (+)RNA Infectious Clones Enabling Their Stable Propagation in *E. coli*", Mar. 2001. Virology, 281(2): 272-280.
Extended European Search Report dated May 26, 2020 for European Patent Application No. 17873411.7, Pushko et al., a counterpart foreign application of U.S. Appl. No. 16/462,383, 7 pages.
Gonzalez, et. al., "Stabilization of a Full-Length Infectious cDNA Clone of Transmissible Gastroenteritis Coronavirus by Insertion of an Intron," May 2002. Journal of Virology, 76(9): 4655-4661.
Johansen, et. al., "Insertion of Introns: A Strategy to Facilitate Assembly of Infectious Full Length Clones." Aug. 2008. Methods in Molecular Biology. doi: 10.1007/978-1-59745-102-4_36, vol. 451, Chapter 36, pp. 535-544.
Schott et al, "Viral and Synthetic RNA Vector Technologies and Applications," Aug. 2016. Molecular Therapy: The Journal of the American Society of Gene Therapy, 24(9): 1512-1527.
Singaporean Office Action dated Sep. 1, 2020 for Singaporean Patent Application No. 11201904365P, Pushko et al., a counterpart foreign application of U.S. Appl. No. 16/462,383, 12 pages.
Indonesia Office Action dated Feb. 25, 2021 for Indonesian Patent Application No. PID201905007, a foreign counterpart to U.S. Appl. No. 16/462,383, 4 pages.

* cited by examiner

*Primary Examiner* — Stacy B Chen
(74) *Attorney, Agent, or Firm* — Lee & Hayes, P.C.

(57) ABSTRACT

Compositions for protecting subjects from diseases caused by (+) SS RNA virus are described herein. The compositions include (i) a vector containing a DNA encoding a RNA molecule of an infectious (+) SS RNA virus operably linked to a eukaryotic RNA polymerase promoter and a carrier; or (ii) (+) SS RNA viruses obtained from eukaryotic cells transfected with the vector of (i) and a carrier.

27 Claims, 11 Drawing Sheets

Specification includes a Sequence Listing.

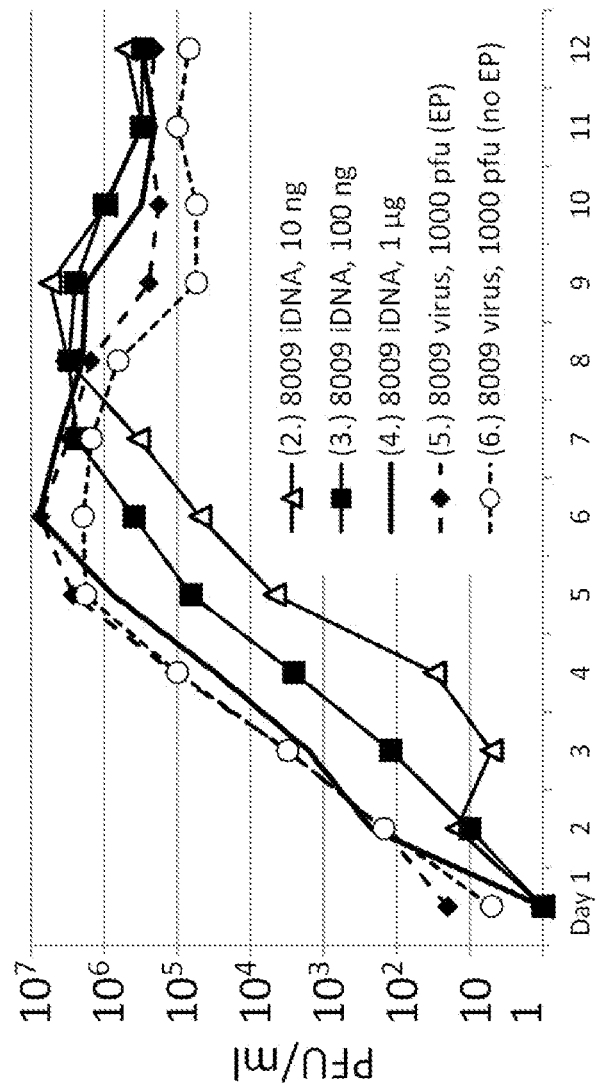
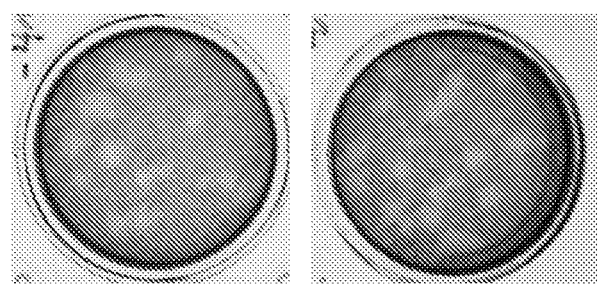
FIGURE 3B
FIGURE 3A

```
   1 TCGCGCGTTT CGGTGATGAC GGTGAAAACC TCTGACACAT GCAGCTCCCG
  51 GAGACGGTCA CAGCTTGTCT GTAAGCGGAT GCCGGGAGCA GACAAGCCCG
 101 TCAGGGCGCG TCAGCGGGTG TTGGCGGGTG TCGGGCTGG CTTAACTATG
 151 CGGCATCAGA GCAGATTGTA CTGAGAGTGC ACCATATGCG GTGTGAAATA
 201 CCGCACAGAT GCGTAAGGAG AAAATACCGC ATCAGGCGCC ATTCGCCATT
 251 CAGGCTGCGC AACTGTTGGG AAGGGCGATC GGTGCGGGCC TCTTCGCTAT
 301 TACGCCAGCT GGCGAAAGGG GGATGTGCTG CAAGGCGATT AAGTTGGGTA
 351 ACGCCAGGGT TTTCCCAGTC ACGACGTTGT AAAACGACGG CCAGTGAATT
 401 CGGCGCGCCT GACATTGATT ATTGACTAGT TATTAATAGT AATCAATTAC
 451 GGGGTCATTA GTTCATAGCC CATATATGGA GTTCCGCGTT ACATAACTTA
 501 CGGTAAATGG CCCGCCTGGC TGACCGCCCA ACGACCCCG CCCATTGACG
 551 TCAATAATGA CGTATGTTCC CATAGTAACG CCAATAGGGA CTTTCCATTG
 601 ACGTCAATGG GTGGAGTATT TACGGTAAAC TGCCCACTTG GCAGTACATC
 651 AAGTGTATCA TATGCCAAGT ACGCCCCTA TTGACGTCAA TGACGGTAAA
 701 TGGCCCGCCT GGCATTATGC CCAGTACATG ACCTTATGGG ACTTTCCTAC
 751 TTGGCAGTAC ATCTACGTAT TAGTCATCGC TATTACCATG GTGATGCGGT
 801 TTTGGCAGTA CATCAATGGG CGTGGATAGC GGTTTGACTC ACGGGGATTT
 851 CCAAGTCTCC ACCCCATTGA CGTCAATGGG AGTTTGTTTT GGCACCAAAA
 901 TCAACGGGAC TTTCCAAAAT GTCGTAACAA CTCCGCCCCA TTGACGCAAA
 951 TGGGCGGTAG GCGTGTACGG TGGGAGGTCT ATATAAGCAG AGCTCTCTGG
1001 CTAACTAGAG agaagtttat ctgtgtgaac ttcttggctt agtatcgtag
1051 agaagaatcg agagattagt gcagtttaaa cagttttta gaacggaaga
1101 taaccatgac taaaaaacca ggagggcccg gtaaaaaccg ggctatcaat
1151 atgctgaaac gcggcctacc ccgcgtattc ccactagtgg gagtgaagag
1201 ggtagtaatg agcttgttgg acggcagagg gccagtacgt ttcgtgctgg
1251 ctcttatcac gttcttcaag tttacagcat tagccccgac caaggcgctt
1301 tcaggccgat ggaaagcagt ggaaaagagt gtggcaatga acatcttac
1351 tagtttcaaa cgagaacttg gaacactcat tgacgccgtg aacaagcggg
1401 gcagaaagca aaacaaaaga ggagGTAAGT ATCAAGGTTA CAAGACAGGT
1451 TTAAGGAGAC CAATAGAAAC TGGGCTTGTC GAGACAGAGA AGACTCTTGC
1501 GTTTCTGATA GGCACCTATT GGTCTTACTG ACATCCACTT TGCCTTTCTC
1551 TCCACAGgaa atgaaggctc aatcatgtgg ctcgcgagct tggcagttgt
1601 catagcttgt gcaggagcca tgaagttgtc gaatttccag gggaagcttt
1651 tgatgaccat caacaacacg gacattgcag acgttatcgt gattcccacc
1701 tcaaaaggag agaacagatg ctgggtccgg gcaatcgacg tcggctacat
1751 gtgtgaggac actatcacgt acgaatgtcc taagcttacc atgggcaatg
1801 atccagagga tgtggattgc tggtgtgaca accaagaagt ctacgtccaa
1851 tatggacggt gcacgcggac caggcattcc aagcgaagca ggagatccgt
1901 gtcggtccaa acacatgggg agagttcact agtgaataaa aagaggctt
1951 ggctggattc aacgaaagcc acacgatatc tcatgaaaac tgagaactgg
2001 atcataagga atcctggcta tgctttcctg gcggcggtac ttggctggat
2051 gcttggcagt aacaacggtc aacgcgtggt atttaccatc ctcctgctgt
2101 tggtcgctcc ggcttacagt tttaattgtc tgggaatggg caatcgtgac
2151 ttcatagaag gagccagtgg agccacttgg gtggacttgg tgctagaagg
2201 agacagctgc ttgacaatca tggcaaacga caaaccaaca ttggacgtcc
```

FIGURE 5A

```
2251 gcatgattaa catcgaagct agccaacttg ctgaggtcag aagttactgc
2301 tatcatgctt cagtcactga catctcgacg gtggctcggt gccccacgac
2351 tggagaagcc cacaacgaga agcgagctga tagtagctat gtgtgcaaac
2401 aaggcttcac tgaccgtggg tggggcaacg gatgtggatt tttcgggaag
2451 ggaagcattg acacatgtgc aaaattctcc tgcaccagta aagcgattgg
2501 gagaacaatc cagccagaaa acatcaaata caaagttggc attttttgtgc
2551 atggaaccac cacttcggaa aaccatggga attattcagc gcaagttggg
2601 gcgtcccagg cggcaaagtt tacagtaaca cccaatgctc cttcggtagc
2651 cctcaaactt ggtgactacg gagaagtcac actggactgt gagccaagga
2701 gtggactgaa cactgaagcg ttttacgtca tgaccgtggg gtcaaagtca
2751 tttctggtcc atagggagtg gtttcatgac ctcgctctcc cctggacgtc
2801 cccttcgagc acagcgtgga gaaacagaga actcctcatg gaatttgaag
2851 gggcgcacgc cacaaaacag tccgttgttg ctcttgggtc acaggaagga
2901 ggcctccatc atgcgttggc aggagccatc gtggtggagt actcaagctc
2951 agtgatgtta acatcaggcc acctgaaatg taggctgaaa atggacaaac
3001 tggctctgaa aggcacaacc tatggcatgt gtacagaaaa attctcgttc
3051 gcgaaaaatc cggtggacac tggtcacgga acagttgtca ttgaactctc
3101 ctactctggg agtgatggcc cctgcaaaat tccgattgtt tccgttgcga
3151 gcctcaatga catgaccccc gttgggcggc tggtgacagt gaaccccttc
3201 gtcgcgactt ccagtgccaa ctcaaaggtg ctggtcgaga tggaaccccc
3251 cttcggagac tcctacatcg tagttggaag gggagacaag cagatcaacc
3301 accattggca caaagctgga agcacgctgg gcaaggcctt ttcaacaact
3351 ttgaagGTAA GGGGCTCACA GTAGCAGGCT TGAGGTCTGG ACATATATAT
3401 GGGTGACAAT GACATCCACT TTGCCTTTCT CTCCACAGgg agctcaaaga
3451 ctggcagcgt tgggcgacac agcctgggac tttggctcta ttggaggggt
3501 cttcaactcc ataggaagag ccgttcacca agtgtttggt ggtgccttca
3551 gaacactctt tgggggaatg tcttggatca cacaagggct aatgggtgcc
3601 ctactgctct ggatgggcgt caacgcacga gaccgatcaa ttgctttggc
3651 cttcttagcc acaggaggtg tgctcgtgtt cttagcgacc aatgtgcatg
3701 ctgacactgg atgtgccatt gacatcacaa gaaaagagat gagatgtgga
3751 agtggcatct tcgtgcacaa cgacgtggaa gcctgggtgg ataggtataa
3801 atatttgcca gaaacgccca gatccctagc gaagatcgtc cacaaagcgc
3851 acaaggaagg cgtgtgcgga gtcagatctg tcactagact ggagcaccaa
3901 atgtgggaag ccgtaaggga cgaattgaac gtcctgctca aagagaatgc
3951 agtggacctc agtgtggttg tgaacaagcc cgtgggaaga tatcgctcag
4001 cccctaaacg cctatccatg acgcaagaga gtttgaaat gggctggaaa
4051 gcatggggaa aaagcatcct ctttgccccg gaattggcta actccacatt
4101 tgtcgtagat ggacctgaga caaggaatg ccctgatgag cacagagctt
4151 ggaacagcat gcaaatcgaa gacttcggct ttggcatcac atcaacccgt
4201 gtgtggctga aaattagaga ggagagcact gacgagtgtg atggagcgat
4251 cataggcacg gctgtcaaag gacatgtggc agtccatagt gacttgtcgt
4301 actggattga gagtcgctac aacgacacat ggaaacttga gagggcagtc
4351 tttggagagG TAAGCCAGCC CAGGCCTCGC CCTCCAGCTC AAGGCGGGAC
4401 AGGTGCCCTA GAGTAGCCTG CATCCAGGGA CAGGCCCAG CCGGGTGCTG
4451 ACACGTCCAC CTCCATCTCT TCCTCAGgtc aaatcttgca cttggccaga
4501 gacacacacc ctttggggag atgatgttga ggaaagtgaa ctcatcattc
4551 cgcacaccat agccggacca aaaagcaagc acaatcggag ggaagggtat
```

FIGURE 5B

```
4601 aagacacaaa accagggacc ttgggatgag aatggcatag tcttggactt
4651 tgattattgc ccagggacaa aagtcaccat tacagaggat tgtagcaaga
4701 gaggcccttc ggtcagaacc actactgaca gtggaaagtt gatcactgac
4751 tggtgctgtc gcagttgctc ccttccgccc ctacgattcc ggacagaaaa
4801 tggctgctgg tacggaatgg aaatcagacc tgttatgcat gatgaaacaa
4851 cactcgtcag atcacaggtt catgctttca aaggtgaaat ggttgaccct
4901 tttcagctgg gccttctggt gatgtttctg gccacccagg aagtccttcg
4951 caagaggtgg acggccagat tgaccattcc tgcggttttg ggggtcctac
5001 ttgtgctgat gcttggggt atcacttaca ctgatttggc gaggtatgtg
5051 gtgctagtcg ctgctgcttt cgcagaggcc aacagtggag gagacgtcct
5101 gcaccttgct ttgattgctg tttttaagat ccaaccagca tttttagtga
5151 tgaacatgct tagcacgaga tggacgaacc aagaaaacgt ggttctggtc
5201 ctaggggctg ccttttccca attggcctca gtagatctgc aaataggagt
5251 ccacggaatc ctgaatgccg ccgctatagc atggatgatt gtccgagcga
5301 tcaccttccc cacaacctcc tccgtcacca tgccagtctt agcgcttcta
5351 actccgggga tgaggctct atacctagac acttacagaa tcatcctcct
5401 cgtcatagg atttgctccc tgctgcacga gaggaaaaag accatggcga
5451 aaaagaaagg agctgtactc ttgggcttag cgctcacatc cactggatgg
5501 ttctcgccca ccactatagc tgccggacta atggtctgca acccaaacaa
5551 gaagagaggg tggccagcta ctgagttttt gtcggcagtt ggattgatgt
5601 ttgccatcgt aggtggtttg gccgagttgg atattgaatc catgtcaata
5651 cccttcatgc tggcaggtct catggcagtg tcctacgtgg tgtcaggaaa
5701 agcaacagat atgtggcttg aacgggccgc cgacatcagc tgggatatgg
5751 gtgctgcaat cacaggaagc agtcggaggc tggatgtgaa actggatgat
5801 gacggagatt ttcacttgat tgatgatccc ggtgttccat ggaaggtctg
5851 ggtcctgcgc atgtcttgca ttggcttagc cgccctcacg ccttgggcca
5901 tcgttcccgc cgctttcggt tattggctca ctttaaaaac aacaaaaaga
5951 gggggcgtgt tttgggacac gccatcccca aaaccttgct caaaaggaga
6001 caccactaca ggagtctacc gaattatggc tagagggatt cttggcactt
6051 accaggccgg cgtcggagtc atgtacgaga atgttttcca cacactatgg
6101 cacacaacta gaggagcagc cattgtgagt ggagaaggaa aattgacgcc
6151 atactggggt agtgtgaaag aagaccgcat agcttacgga ggcccatgga
6201 ggtttgaccg aaaatggaat ggaacagatg acgtgcaagt gatcgtggta
6251 gaaccgggga agggcgcagt aaacatccag acaaaaccag gagtgtttcg
6301 gactcccttc ggggaggttg gggctgttag tctggattac ccgcgaggaa
6351 catccggctc acccattctg gattccaatg gagacattat aggcctatac
6401 ggcaatggag ttgagcttgg cgatggctca tacgtcagcg ccatcgtgca
6451 gggtgaccgt caggaggaac cagtcccaga agcttacacc ccaaacatgt
6501 tgagaaagag acagatgact gtgctagatt gcaccctgg ttcagggaaa
6551 accaggaaaa ttctgccaca aataattaag gacgctatcc agcagcgcct
6601 aagaacagct gtgttggcac cgacgcgggt ggtagcagca gaaatggcag
6651 aagctttgag agggctccca gtacgatatc aaacttcagc agtgcagaga
6701 gagcaccaag ggaatgaaat agtggatgtg atgtgccacg ccactctgac
6751 ccatagactg atgtcaccga acagagtgcc caactacaac ctatttgtca
6801 tggatgaagc tcatttcacc gacccagcca gtatagccgc acgaggatac
6851 attgctacca aggtggaatt aggggaggca gcagccatct ttatgacagc
6901 gaccccgcct ggaaccacgg atcctttcc tgactcaaat gccccaatcc
```

FIGURE 5C

```
6951 atgatttgca agatgagata ccagacaggg catggagcag tggatacgaa
7001 tggatcacag aatatgcggg taaaaccgtg tggtttgtgg cgagcgtaaa
7051 aatggggaat gagattgcaa tgtgcctcca aagagcgggg aaaaaggtca
7101 tccaactcaa ccgcaagtcc tatgacacag aatacccaaa atgtaagaat
7151 ggagactggg attttgtcat taccaccgac atctctgaaa tgggggccaa
7201 cttcggtgcg agcagggtca tcgactgtag aaagagcgtg aaacccacca
7251 tcttagaaga gggagaaggc agagtcatcc tcggaaaccc atctcccata
7301 accagtgcaa gcgcagctca acggaggggc agagtaggca gaaaccccaa
7351 tcaagttgga gatgaatacc actatggggg ggctaccagt gaagatgaca
7401 gtaacctagc ccattggaca gaggcaaaga tcatgttaga caacatacac
7451 atgcccaatg gactggtggc ccagctctat ggaccagaga gggaaaaggc
7501 tttcacaatg gatggcgaat accgtctcag aggtgaagaa aagaaaaact
7551 tcttagagct gcttaggacg gctgacctcc cggtgtggct ggcctacaag
7601 gtggcgtcca atggcattca gtacaccgac agaaagtggt gttttgatgg
7651 gccgcgtacg aatgccatac tggaggacaa caccgaggta gagatagtca
7701 cccggatggg tgagaggaaa atcctcaagc cgagatggct tgatgcaaga
7751 gtttatgcag atcaccaggc cctcaagtgg ttcaaagact tgcagcagg
7801 gaagagatca gccgttagct tcatagaggt gctcggtcgc atgcctgagc
7851 atttcatggg aaagacgcgg gaagctttag acaccatgta cttggttgca
7901 acggctgaga aaggtgggaa agcacaccga atggctctcg aagagctgcc
7951 agatgcactg gaaaccatca cacttattgt cgccattact gtgatgacag
8001 gaggattctt cctactaatg atgcagcgaa agggtatagg gaagatgggt
8051 cttggagctc tagtgctcac actagctacc ttcttcctgt gggcggcaga
8101 ggttcctgga accaaaatag cagggaccct gctgatcgcc ctgctgctga
8151 tggtggttct catcccagaa ccggaaaaac agaggtcaca gacagataac
8201 caactggcgg tgtttctcat ctgtgtcttg accgtggttg gagtggtggc
8251 agcaaacgag tacgggatgc tagaaaaaac caaagcggat ctcaagagca
8301 tgtttggcgg aaagacgcag gcatcaggac tgactggatt gccaagcatg
8351 gcactggacc tgcgtccagc cacagcctgg gcactgtatg ggggagcac
8401 agtcgtgcta acccctcttc tgaagcacct gatcacgtcg aatacgtca
8451 ccacatcgct agcttcaatt aactcacaag ctggctcatt attcgtcttg
8501 ccacgaggcg tgccttttac cgacctagac ttgactgttg gcctcgtctt
8551 ccttggctgt tggggtcaag tcaccctcac aacgtttctg acagccatgg
8601 ttctggcgac acttcactat gggtacatgc tccctggatg gcaagcagaa
8651 gcactcaggg ctgcccagag aaggacagcg gctggaataa tgaagaatgc
8701 cgttgttgac ggaatggtcg ccactgatgt gcctgaactg gaaaggacta
8751 ctcctctgat gcaaagaaa gtcggacagg tgctcctcat aggggtaagc
8801 gtggcagcgt tcctcgtcaa ccctaatgtc accactgtga gagaagcagg
8851 ggtgttggtg acggcggcta cgcttacttt gtgggacaat ggagccagtg
8901 ccgtttggaa ttccaccaca gccacgggac tctgccatgt catgcgaggt
8951 agctacctgg ctggaggctc cattgcttgg actctcatca gaacgctga
9001 taagccctcc ttgaaaggg gaaggcctgg gggcaggacg ctaggggagc
9051 agtggaagga aaaactaaat gccatgagta gagaagagtt ttttaaatac
9101 cggagagagg ccataatcga ggtggaccgc actgaagcac gcagggccag
9151 acgtgaaaat aacatagtgg gaggacatcc ggtttcgcga ggctcagcaa
9201 aactccgttg gctcgtggag aaaggatttg tctcgccaat aggaaaagtc
9251 attgatctag ggtgtgggcg tggaggatgg agctactacg cagcaaccct
```

FIGURE 5D

```
9301  gaagaaggtc caggaagtca gaggatacac gaaaggtggg gcgggacatg
9351  aagaaccgat gctcatgcag agctacggct ggaacctggt ctccctgaag
9401  agtggagtgg acgtgtttta caaaccttca gagcccagtg atacccgtgtt
9451  ctgtgacata ggggaatcct ccccaagtcc agaagtagaa gaacaacgca
9501  cactacgcgt cctagagatg acatctgact ggttgcaccg aggacctaga
9551  gagttctgca ttaaagttct ctgcccttac atgcccaagg ttatagaaaa
9601  aatggaagtt ctgcagcgtc gcttcggagg tgggctagtg cgtctccccc
9651  tgtcccgaaa ctccaatcac gagatgtatt gggttagtgg agccgctggc
9701  aatgtggtgc acgctgtgaa catgaccagc caggtattac tggggcgaat
9751  ggatcgcaca gtgtggagag ggccaaagta tgaggaagat gtcaacctag
9801  ggagcggaac aagagccgtg ggaaagggag aagtccatag caatcaggag
9851  aaaatcaaga agagaatcca gaagcttaaa gaagaattcg ccacaacgtg
9901  gcacaaagac cctgagcatc cataccgcac ttggacatac cacggaagct
9951  atgaagtgaa ggctactggc tcagccagct ctctcgtcaa cggagtggtg
10001 aagctcatga gcaaaccttg gacgccatt gccaacgtca ccaccatggc
10051 catgactgac accaccccttt tggacagca aagagttttc aaggagaaag
10101 ttgacacgaa ggctcctgag ccaccagctg gagccaagga agtgctcaac
10151 gagaccacca actggctgtg ggcctacttg tcacgggaaa aaagaccccg
10201 cttgtgcacc aaggaagaat tcattaagaa agttaacagc aacgcggctc
10251 ttggagcagt gttcgctgaa cagaatcaat ggagcacggc gcgtgaggct
10301 gtggatgacc cgcggttttg ggagatggtt gatgaagaga gggaaaacca
10351 tctgcgagga gagtgtcaca catgtatcta caacatgatg ggaaaaagag
10401 agaagaagcc tggagagttt ggaaaagcta aggaagcag ggccatttgg
10451 ttcatgtggc ttggagcacg gtatctagag tttgaagctt tggggttcct
10501 gaatgaagac cattggctga gccgagagaa ttcaggaggt ggagtggaag
10551 gctcaggcgt ccaaaagctg ggatacatcc tccgtgacat agcaggaaag
10601 caaggaggga aaatgtacgc tgatgatacc gccggtgggg acactagaat
10651 taccagaact gatttagaaa atgaagctaa ggtactggag ctcctagacg
10701 gtgaacaccg catgctcgcc cgagccataa ttgaactgac ttacaggcac
10751 aaagtggtca aggtcatgag acctgcagca gaaggaaaga ccgtgatgga
10801 cgtgatatca agagaagatc aaaggggggag tggacaggtg gtcacttatg
10851 ctcttaacac tttcacgaac atcgctgtcc agctcgtcag gctgatggag
10901 gctgaggggg tcattggacc acaacacttg gaacatctac ctaggaaaaa
10951 caagatagct gtcaggacct ggctctttga gaatggagag gagagagtga
11001 ccaggatggc gatcagcgga gacgactgtg ccgtcaaacc gctggacgac
11051 agattcgcca cagccctcca cttcctcaac gcaatgtcaa aggtcagaaa
11101 agacatccag gaatggaagc cttcgcatgg ctggcacgat tggcagcaag
11151 ttcccttctg ttctaaccat tttcaggaga ttgtgatgaa agatggaagg
11201 agtatagttg tcccgtgcag aggacaggat gagctgatag cagggctcg
11251 catctctcct ggagctggat ggaatgtgaa ggacacagct tgcctggcca
11301 aagcatatgc acagatgtgg ctactcctat acttccatcg cagggacttg
11351 cgtctcatgg caaatgcgat ttgctcagca gtgccagtag attgggtgcc
11401 cacaggcagg acatcctggt caatacactc gaaaggagag tggatgacca
11451 cggaagacat gctgcaggtc tggaacagag tttggattga agaaaatgaa
11501 tggatgatgg acaagactcc aatcacaagc tggacagacg ttccgtatgt
11551 gggaaagcgc gaggacatct ggtgtggcag cctcatcgga acgcgatcca
11601 gagcaacctg ggctgagaac atctatgcgg cgataaacca ggttagagct
```

```
11651 gtcattggga aagaaaatta tgttgactac atgacctcac tcaggagata
11701 cgaagacgtc ttgatccagg aagacagggt catctagtgt gatttaaggt
11751 agaaaagtag actatgtaaa caatgtaaat gagaaaatgc atgcatatgg
11801 agtcaggcca gcaaaagctg ccaccggata ctgggtagac ggtgctgcct
11851 gcgtctcagt cccaggagga ctgggttaac aaatctgaca acagaaagtg
11901 agaaagccct cagaaccgtc tcggaagtag gtccctgctc actggaagtt
11951 gaaagaccaa cgtcaggcca caaatttgtg ccactccgct agggagtgcg
12001 gcctgcgcag ccccaggagg actgggttac caaagccgtt gaggccccca
12051 cggcccaagc ctcgtctagg atgcaataga cgaggtgtaa ggactagagg
12101 ttagaggaga ccccgtggaa acaacaacat gcggcccaag cccctcgaa
12151 gctgtagagg aggtggaagg actagaggtt agaggagacc ccgcatttgc
12201 atcaaacagc atattgacac ctgggaatag actgggagat cttctgctct
12251 atctcaacat cagctactag gcacagagcg ccgaagtatg tagctggtgg
12301 tgaggaagaa cacaggatct CTCGAGtggg tcggcatggc atctccacct
12351 cctcgcggtc cgacctgggc atccgaagga ggacgcacgt ccactcggat
12401 ggctaaggga gagccacgag ctcctcgaca gatcataatc agccatacca
12451 catttgtaga ggttttactt gctttaaaaa acctcccaca cctcccctg
12501 aacctgaaac ataaaatgaa tgcaattgtt gttgttaact tgtttattgc
12551 agcttataat ggttacaaat aaagcaatag catcacaaat ttcacaaata
12601 aagcattttt ttcactgcat tctagttgtg gtttgtccaa actcatcaag
12651 atgtatacAA GCTTGGTGTA ATCATGGTCA TAGCTGTTTC CTGTGTGAAA
12701 TTGTTATCCG CTCACAATTC CACACAACAT ACGAGCCGGA AGCATAAAGT
12751 GTAAAGCCTG GGGTGCCTAA TGAGTGAGCT AACTCACATT AATTGCGTTG
12801 CGCTCACTGC CCGCTTTCCA GTCGGGAAAC CTGTCGTGCC AGCTGCATTA
12851 ATGAATCGGC CAACGCGCGG GGAGAGGCGG TTTGCGTATT GGGCGCTCTT
12901 CCGCTTCCTC GCTCACTGAC TCGCTGCGCT CGGTCGTTCG GCTGCGGCGA
12951 GCGGTATCAG CTCACTCAAA GGCGGTAATA CGGTTATCCA CAGAATCAGG
13001 GGATAACGCA GGAAAGAACA TGTGAGCAAA AGGCCAGCAA AAGGCCAGGA
13051 ACCGTAAAAA GGCCGCGTTG CTGGCGTTTT TCCATAGGCT CCGCCCCCCT
13101 GACGAGCATC ACAAAAATCG ACGCTCAAGT CAGAGGTGGC GAAACCCGAC
13151 AGGACTATAA AGATACCAGG CGTTTCCCCC TGGAAGCTCC CTCGTGCGCT
13201 CTCCTGTTCC GACCCTGCCG CTTACCGGAT ACCTGTCCGC CTTTCTCCCT
13251 TCGGGAAGCG TGGCGCTTTC TCATAGCTCA CGCTGTAGGT ATCTCAGTTC
13301 GGTGTAGGTC GTTCGCTCCA AGCTGGGCTG TGTGCACGAA CCCCCCGTTC
13351 AGCCCGACCG CTGCGCCTTA TCCGGTAACT ATCGTCTTGA GTCCAACCCG
13401 GTAAGACACG ACTTATCGCC ACTGGCAGCA GCCACTGGTA ACAGGATTAG
13451 CAGAGCGAGG TATGTAGGCG GTGCTACAGA GTTCTTGAAG TGGTGGCCTA
13501 ACTACGGCTA CACTAGAAGA ACAGTATTTG GTATCTGCGC TCTGCTGAAG
13551 CCAGTTACCT TCGGAAAAAG AGTTGGTAGC TCTTGATCCG GCAAACAAAC
13601 CACCGCTGGT AGCGGTGGTT TTTTGTTTG CAAGCAGCAG ATTACGCGCA
13651 GAAAAAAGG ATCTCAAGAA GATCCTTTGA TCTTTTCTAC GGGGTCTGAC
13701 GCTCAGTGGA ACGAAAACTC ACGTTAAGGG ATTTTGGTCA TGAGATTATC
13751 AAAAAGGATC TTCACCTAGA TCCTTTTAAA TTAAAAATGA AGTTTTAAAT
13801 CAAGCCCAAT CTGAATAATG TTACAACCAA TTAACCAATT CTGATTAGAA
13851 AAACTCATCG AGCATCAAAT GAAACTGCAA TTTATTCATA TCAGGATTAT
13901 CAATACCATA TTTTTGAAAA AGCCGTTTCT GTAATGAAGG AGAAAACTCA
13951 CCGAGGCAGT TCCATAGGAT GGCAAGATCC TGGTATCGGT CTGCGATTCC
```

FIGURE 5F

```
14001 GACTCGTCCA ACATCAATAC AACCTATTAA TTTCCCCTCG TCAAAAATAA
14051 GGTTATCAAG TGAGAAATCA CCATGAGTGA CGACTGAATC CGGTGAGAAT
14101 GGCAAAAGTT TATGCATTTC TTTCCAGACT TGTTCAACAG GCCAGCCATT
14151 ACGCTCGTCA TCAAAATCAC TCGCATCAAC CAAACCGTTA TTCATTCGTG
14201 ATTGCGCCTG AGCGAGACGA AATACGCGAT CGCTGTTAAA AGGACAATTA
14251 CAAACAGGAA TCGAATGCAA CCGGCGCAGG AACACTGCCA GCGCATCAAC
14301 AATATTTTCA CCTGAATCAG GATATTCTTC TAATACCTGG AATGCTGTTT
14351 TTCCGGGGAT CGCAGTGGTG AGTAACCATG CATCATCAGG AGTACGGATA
14401 AAATGCTTGA TGGTCGGAAG AGGCATAAAT TCCGTCAGCC AGTTTAGTCT
14451 GACCATCTCA TCTGTAACAT CATTGGCAAC GCTACCTTTG CCATGTTTCA
14501 GAAACAACTC TGGCGCATCG GCTTCCCAT  ACAAGCGATA GATTGTCGCA
14551 CCTGATTGCC CGACATTATC GCGAGCCCAT TTATACCCAT ATAAATCAGC
14601 ATCCATGTTG GAATTTAATC GCGGCCTCGA CGTTTCCCGT TGAATATGGC
14651 TCATAACACC CCTTGTATTA CTGTTTATGT AAGCAGACAG TTTTATTGTT
14701 CATGATGATA TATTTTTATC TTGTGCAATG TAACATCAGA GATTTGAGA
14751 CACGGGCCAG AGCTGCA
```

FIGURE 5G

VACCINES AGAINST INFECTIOUS DISEASES CAUSED BY POSITIVE STRANDED RNA VIRUSES

CROSS REFERENCE TO RELATED APPLICATIONS

This application is the U.S. National Phase Application of International Application No. PCT/US2017/062733, filed Nov. 21, 2017, which claims the benefit of U.S. Provisional Application 62/426,708, filed Nov. 28, 2016, which are hereby incorporated by reference in their entirety.

FIELD

Compositions for protecting subjects against diseases caused by positive sense single stranded RNA viruses are described.

BACKGROUND

A virus is a small non-cellular organism composed of genetic material and protein. There are different types of viruses. For example, a virus can be a DNA virus which replicates in the nucleus of a host, or a RNA virus which replicates in the cytoplasm of a cell. A virus can be double stranded or single stranded. Moreover, a single stranded RNA virus can be positive (+, sense) stranded or negative (−) stranded. These different types of viruses cause various viral infections.

A viral infection occurs when a pathogenic virus invades an organism's body. Once inside, the virus reproduces by attaching itself to a cell and reprogramming the cell to replicate new viruses until the cell burst and die enabling viruses to spread rapidly causing various infectious diseases in human and animals. Infectious diseases caused by viruses include the common cold, flu, and warts. However, viruses also cause severe diseases such as AIDS, small pox, herpes, hemorrhagic fever, polio, measles, mumps, and rubella.

Vaccines have been developed and have successfully reduced the incidence of as polio, measles, mumps and rubella. Conventional vaccines contain live viruses that have been attenuated. However, because these viruses have the potential to revert to more pathogenic phenotypes and may be under-attenuated in immunocompromised hosts, there is the need to develop a safe, immunogenic vaccine, which induces lasting immunity in a wide variety of viral systems.

In recent years, iDNA® (Medigen, Inc.) vaccines, which generate live attenuated viruses in vivo, have been developed. Full-length cDNA of many RNA viruses has been cloned into *E. coli* plasmids to produce iDNA® vaccines. However, in many cases, it has been difficult to prepare such plasmids, because full-length virus cDNA is often toxic in *E. coli* and cannot be prepared in large quantities.

SUMMARY

Vectors comprising a DNA encoding a RNA molecule of an infectious (+)SS RNA virus operably linked to a suitable promoter for expression in a cell, especially a eukaryotic cell, are described herein. The infectious (+)SS RNA virus can be a chimeric virus encoded by the RNA sequence of at least two different (+)SS RNA viruses.

A homogeneous population of clonally purified (+)SS RNA viruses obtained by transfecting the vectors described above into eukaryotic cells is also described herein.

Compositions including the vectors or the homogeneous population of clonally purified (+)SS RNA viruses and a carrier are described herein. Also described are pharmaceutical compositions comprising the vectors and a pharmaceutically acceptable carrier.

The present disclosure also describes vaccines including the vectors and vaccines including a homogeneous population of clonally purified (+)SS RNA viruses. The vectors of the vaccine include DNA encoding the RNA molecule of a nonpathogenic and/or attenuated (+)SS RNA virus. The homogeneous population of clonally purified (+)SS RNA viruses of a vaccine are nonpathogenic and/or attenuated (+)SS RNA viruses. Moreover, the present disclosure describes methods of using the vaccines to immunize and to protect subjects against diseases caused by infectious (+)SS RNA viruses are also described herein.

Further, the present disclosure describes methods of using the vector described herein to make vaccines and to obtain a homogenous populations of clonally purified (+)SS RNA viruses. Furthermore the present disclosure describes methods of using the vector to obtain host cells transfected with a vector described herein.

BRIEF DESCRIPTION OF THE DRAWINGS

FIGS. 3A and 3B show detection of JEV virus in the medium from Vero cells transfected with pMG8009 iDNA® plasmid. (A) Plaque assay in BHK cells. Upper panel, plaque assay of growth medium from virus-infected Vero cells (no electroporation), sample taken on day 7 post infection with 1000 PFU (sample #6 on FIG. 3B). Lower panel, plaque assay of growth medium from pMG8009-transfected Vero cells (after electroporation), sample taken on day 7 post transfection with 10 ng of DNA (sample #2 on FIG. 3B). (B) Growth curves of JEV virus in the medium of Vero cells transfected with pMG8009 iDNA® (samples 2, 3, 4) or infected with pMG8009-derived virus (samples 5 and 6). Samples 5 and 6 show infection with 1000 PFU of pMG8009-derived vaccine virus of electroporated and nonelectroporated Vero cells, respectively, to detect if electroporation procedure affects growth of the virus in Vero cells.

FIGS. 5A-5G show the nucleotide sequence (SEQ ID NO: 1) of the pMG8009 plasmid which includes the cDNA encoding the full length genomic RNA of JEV (strain SA14-14-2) operably linked to the CMV immediate-early promoter and inserted into pUC backbone plasmid. The nucleotides of the pUC plasmid and introns are in upper case letters. The CMV promoter is in italics. The cDNA encoding the genomic RNA of JEV is in bold. The introns are underlined.

DETAILED DESCRIPTION

Figure 1A:
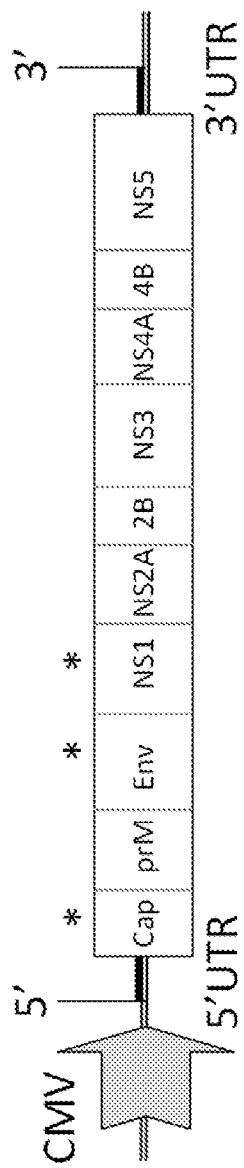
FIGS. 1A and 1B show preparation of pMG8009 JEV DNA vaccine containing synthetic cDNA of SA-14-14-2 JEV strain. (A) DNA construct is schematically depicted including CMV promoter, full-length JEV SA14-14-2 synthetic cDNA and three synthetic introns. Locations of CMV promoter, JEV genes and introns 1-3 (asterisks) are shown schematically not to scale. (B) Result of 1% gel electrophoresis of plasmid DNA isolated from ten independent *E. coli* colonies. The pMG8009 was transformed into chemically competent *E. coli* Stbl3 cells and grown on LB agar plate containing 50 µg/ml kanamycin. Ten independent colonies from the plate were grown in 2 ml LB cultures and DNA was isolated and resuspended in 50 µl of sterile water. 1 µl of the resulting plasmid DNA was loaded on 1% TAE agarose gel.

The present disclosure provides vaccines to protect against diseases caused by RNA viruses, particularly, (+)SS RNA viruses. The families of (+)SS RNA viruses include Astroviridae, Caliciviridae, Picornaviridae, Coronoviridae, Retroviridae, Togaviridae, and Flaviviridae. As examples, the Astroviridae family includes the human astrovirus; the Caliciviridae family includes the Norwalk virus; the Picornaviridae family includes the coxsackievirus, the Hepatitis A virus, the poliovirus, and the rhinovirus; the Coronoviridae family includes the coronavirus and the SAR virus; the Retroviridae family includes the alpharetrovirus, the betaretrovirus, the deltaretrovirus, the lentivirus, and the spumavirus; the Togaviridae family includes the Rubella virus and the alpha virus; and the flaviviridae family includes the Hepatitis C virus and the flavivirus.

In embodiments, the vaccines described herein protect against diseases caused by alphaviruses. Alphaviruses include the Barmah Forest virus, the Eastern equine encephalitis virus, the Chikungunya virus, the O'Nyong Nyong virus, the Ross River virus, the Semliki Forest virus, the Panama virus, the Venezuelan equine encephalitis virus, the Western equine encephalitis virus, and the Sindbis virus.

In embodiments, the vaccines described herein protect against diseases caused by flaviviruses. Flaviviruses include the Yellow fever virus, the Dengue virus, the West Nile virus, the Zika virus, the tick borne encephalitis virus, and the Japanese encephalitis virus.

As is well-known, (+)SS RNA viruses cause various diseases including viral gastroenteritis, hepatitis A, hepatitis C, Dengue fever, Yellow fever, West Nile fever, polio, severe acute respiratory syndrome virus (SARS), encephalitis, measles, mumps, rubella, and foot and mouse disease. As used herein, the term "disease caused by (+)SS RNA viruses" includes infections caused by (+)SS RNA viruses.

In embodiments, the vaccines described herein protect against encephalitis, for example, encephalitis caused by JEV.

The vaccines described herein include a therapeutically effective amount of (i) a vector including DNA encoding a RNA of an infectious (+)SS RNA virus, such as a plasmid DNA encoding a RNA of an infectious (+)SS RNA virus; or (ii) a homogeneous population of clonally purified infectious (+)SS RNA viruses obtained from cells transfected with the vector of (i). Moreover, the DNA contained in the vector encodes a nonpathogenic and/or attenuated (+)SS RNA virus and the DNA includes a suitable promoter for expression in eukaryotic cells.

As used herein, the term "infectious" virus refers to a virus that can invade a cell, reproduce (replicate), and multiply. An infectious virus can cause a disease or multiply unnoticed. Therefore, an infectious (replicating) virus can be pathogenic or nonpathogenic. In embodiments, the infectious virus is nonpathogenic and/or attenuated when used in a vaccine. An infectious (+)SS RNA virus includes a virus encoded by its full-length RNA genomic sequence. In particular embodiments, the present disclosure provides infectious DNA (iDNA®) vaccines which generate live viruses for protecting a subject against diseases caused by (+)SS RNA viruses.

In contrast to conventional DNA vaccines, iDNA® vaccines generate DNA-launched live attenuated viruses in vivo. Conventional DNA vaccines only contain a sequence of DNA encoding a specific gene of interest, whereas iDNA® vaccines include DNA encoding the entire functional genomic RNA of the (+)SS RNA virus. Moreover, unlike (+)SS RNA viruses which replicate in the cytoplasm of a host cell and do not enter the nucleus of a host cell, the DNA of a iDNA® vaccine enters the nucleus of a host cell for initiation of replication. When the DNA of a iDNA® vaccine is injected into a host cell, the DNA enters the nucleus which transcribes the entire genomic RNA of the infectious (+)SS RNA virus for replication. The transcribed functional genomic RNA of the infectious (+)SS RNA virus is subsequently transported into the cytoplasm of the host cell for replication and multiplication to obtain a virus progeny. This process reduces the possibly of mutations and reversions, commonly found with vaccine production.

Similar to conventional DNA vaccines, iDNA® vaccines are inexpensive and simple to manufacture. Moreover, iDNA® vaccines induce immunity rapidly because live attenuated viruses can be produced at the site of administration of the vaccine in a subject. Also, only a single small dose is required to induce immunity because live attenuated viruses are produced. Additionally, the iDNA® vaccines generate a genetically stable and homogeneous population of clonally purified attenuated (+)SS RNA viruses in vivo, which improves vaccine safety.

Further, the iDNA® technology can be used to a generate genetically stable and homogeneous population of clonally purified attenuated (+)SS RNA viruses for use as vaccines. Because (+) SS RNA virus is launched from genetically stable iDNA®, the iDNA® technology can reduce the possibility of genetic mutagenesis of the RNA of a (+)SS RNA virus by at least about 50%, 70%, 80%, 90%, or 99%. In embodiments, the present disclosure describes vaccines including a homogeneous population of attenuated (+)SS RNA viruses.

iDNA® technology is based on the use of a DNA vector to generate vaccines in vitro or in vivo. The term "vector" and "plasmid" are used interchangeably throughout. In embodiments, the present disclosure provides a vector including a DNA encoding a RNA molecule operably linked to a suitable promoter for expression in a cell, such as a eukaryotic cell. In embodiments, the DNA is a cDNA molecule encoding the full-length (genomic) RNA of (+)SS RNA virus. In embodiments, the RNA molecule encodes an infectious (+)SS RNA virus. The DNA molecule includes at least three introns. At least one of the introns is located in a gene (or a region of the DNA) encoding a non-structural protein of the (+)SS RNA virus and one intron is located in a gene (or a region of the DNA) encoding a structural protein of the (+)SS RNA virus.

The vector described herein include regulatory elements in addition to the DNA encoding the RNA molecule. Regulatory elements include for example, one or more promoters, poly A tail, terminators, enhancers, ribozymes, internal ribosomal entry site, or nuclear transport element. The promoters include those suitable for expression in host cells. In embodiments, the promoter is suitable for expression in eukaryotic cells, for example mammalian cells. An example of such a promoter is a eukaryotic RNA polymerase promoter. Other examples of promoters for expression of the vector in eukaryotic cells include CMV, RSV, SV40, HSV, Human Pol I, Human Pol II, and Human Pol III. In particular embodiments, the promoter is a CMV promoter.

The location of the promoter relative to the transcription start site in the vector is important. As an example, the promoter can be placed from about 5 to about 100, about 10 to about 50, or about 10 to about 20 nucleotides upstream of the 5' end of the DNA encoding the RNA molecule. In embodiments, the vector described herein includes a CMV promoter which is located at about 12 to about 18 nucleotides upstream of the 5' end of the DNA encoding the RNA molecule. In particular embodiments, the optimal position of the CMV promoter is about 15 nucleotides upstream of the 5' end of the DNA encoding the RNA molecule.

In embodiments, the poly A tail is located from about 0 to 500 nucleotides downstream from the 3' end of the DNA encoding the RNA molecule.

In embodiments, the vector also includes elements that ensure synthesis and transport of the transcribed RNA molecule from the nucleus to the cytoplasm of the cell.

In embodiments, the DNA contained in the vector encodes a RNA molecule, which encodes an infectious (+)SS RNA virus. In particular embodiments, the infectious (+)SS RNA virus is a nonpathogenic and/or attenuated virus.

In embodiments, the infectious (+)SS RNA virus is a flavivirus. Examples of flavivirus includes JEV, Dengue virus, Yellow fever virus, West Nile virus, and Zika virus. In embodiments, the flavivirus is JEV. The JEV is a nonpathogenic virus. In particular embodiments, the JEV is a nonpathogenic and/or attenuated virus. An example of an attenuated JEV is the SA14-14-2 strain, GenBank Acc No. AF315119.

Modifications can be made to the DNA encoding the RNA of an infectious (+)SS RNA virus to attenuate a strain or further improve the attenuation of a strain. The DNA can be modified to ensure sufficient attenuation and/or to introduce other characteristics, while still maintaining infectivity and the desired therapeutic effect. Optimization of attenuation can improve the vaccine and reduce adverse effects associated with vaccination. In embodiments, the DNA encoding the RNA of an infectious (+)SS RNA virus can be modified by insertion, deletion, and/or substitution of one or more of the nucleic acids. As an example, the modified DNA can have at least about 50%, 60%, 70%, 80%, 90%, 95%, or 97% or 99% sequence identity with the wild type sequence encoding the infectious (+)SS RNA virus.

Moreover, the use of iDNA technology generates naturally attenuated viruses. These viruses generated by iDNA technology are attenuated as compared to the original wild-type or naturally occurring virus. Moreover, these viruses are attenuated at least 20% more than attenuated viruses prepared by conventional methods (Poirier et al. 2017), as determined based on the number of subjects after injection with such virus population. The present disclosure describes (+)SS RNA virus generated by iDNA technology described herein that are attenuated by at least about 5%, 10%, 15%, 20%, 25%, or 30% more than attenuated viruses prepared by the conventional method.

The DNA contained in the vector encodes a RNA molecule of an infectious (+)SS RNA virus that is nonpathogenic and/or attenuated. In embodiments, the DNA contained in the vector encodes an infectious JEV, Dengue fever virus, Yellow fever virus, West Nile virus, or Zika virus that is nonpathogenic and/or attenuated.

The DNA contained in the vector can also encode a chimeric RNA molecule that includes the RNA of at least two different (+)SS RNA viruses. The RNA of the second (+)SS RNA virus replaces a portion of the full length RNA encoding the first (+)SS RNA virus. Thus, the chimeric RNA molecule encodes an infectious chimeric (+)SS RNA virus and can be nonpathogenic and/or attenuated. In embodiments, the DNA contained in the vector encodes a chimeric (+)SS RNA virus including RNA from at least two different (+)SS RNA viruses of the same genus. As an example, the first (+)SS RNA virus is a flavivirus and the second (+)SS RNA virus is another flavivirus. As another example, the first (+)SS RNA virus is JEV, while the second (+)SS RNA virus is the Dengue virus, the Yellow Fever virus, the West Nile virus, or the Zika virus. In embodiments, the DNA encodes a chimeric RNA molecule which includes the RNA of the JEV and Zika virus. Other examples include DNA encoding chimeric RNA molecule of Yellow fever virus and Dengue fever virus, or Yellow fever virus and Zika virus, or Yellow fever virus and Zika virus, or Yellow fever virus and West Nile virus. Such DNA vectors encoding chimeric viruses would induce immune response and protect from infection with either one flavivirus, or from two or more flaviviruses.

The chimeric RNA molecule can contain at least about 50%, 55%, 60%, 65%, 70%, 75%, 80%, or 85% of the nucleic acid sequence from a first (+)SS RNA virus.

The present disclosure describes insertion of introns into the DNA encoding the (+)SS RNA molecule to improve the stability of the DNA in host cells and to improve yields of the DNA in the host cells, particularly E. coli that is used for propagation of iDNA plasmid encoding the (+)SS RNA virus described herein. In embodiments, the DNA encoding the RNA molecule includes three introns. The term "intron" refers to a fragment of DNA encoding intron RNA that does not code for a protein and interrupts the sequence of the gene and can be subsequently removed by a splicing mechanism to restore the gene sequence. An intron can contain a stop codon or several stop codons. Examples of stop codons in a DNA include TAA, TAG, and TGA. Other known introns can also be used. In particular embodiments, the intron sequences in the DNA described herein are derived from mouse immunoglobulin H chain V-region precursor gene (Genbank accession M12880).

In embodiments, the DNA contains at least three introns, at least four introns, at least five introns, at least six introns, at least seven introns, at least eight introns, at least nine introns, or at least ten introns. The placement of the introns can be determined empirically or by predicting promoters using methods known in the art (Shahmuradov 2017). At least one of the introns is inserted in the gene encoding a non-structural (NS) protein of a (+)SS RNA virus, and at least one of the introns is inserted in the gene encoding a structural protein.

(+)SS RNA viruses include structural and non-structural genes. As an example, the non-structural proteins of a flavivirus include the NS1, NS2A, NS2B, NS3, NS4A, 2K, NS4B, and NS5 proteins. The structural proteins of a flavivirus include the capsid (Cap), the membrane (prM/M), and the envelope (Env) proteins. In embodiments, at least one of the introns is inserted in a gene encoding the NS1, NS2A, NS2B, NS3, NS4A, 2K, NS4B, or NS5 protein of a flavivirus, and at least one of the introns is inserted in a gene encoding the Cap, the Env, or the prM/M protein of a flavivirus. These structural and non-structural proteins of the flavivirus are part of a polyprotein that is encoded by the structural and non-structural genes of the flavivirus.

In embodiments, the flavivirus is the attenuated JEV SA14-14-2 strain and the nucleotide sequence of the JEV SA14-14-2 strain is provided at GenBank Acc No. (GB Acc.) AF315119.1. As shown in Table 1 below, nucleotides 96 to 2477 (of GB Acc. AF315119.1) encode the structural proteins (Cap, prM/M, and Env), and nucleotides 2478 to 10391 encode the non-structural proteins (NS1, NS2A, NS2B, NS3, NS4A, NS4B, and NS5). In other embodiments, at least one of the introns is inserted between nucleotides 96-2477, and at least one intron is inserted between nucleotides 2478 to 10391 of GB Acc. AF315119.1. In particular embodiments, the introns are inserted immediately after nucleotide 414 (capsid), 2213 (envelope) and 3134 of the nucleotide sequence of the JEV strain SA14-14-2 provided at GenBank Acc No. AF315119.

In embodiments, the flavivirus is the Yellow Fever YF17D strain and the nucleotide sequence of the YF17D strain is provided at GB Acc. X03700.1. As shown in Table 1 below, nucleotides 122 to 2452 (of GB Acc. X03700.1 encode the structural proteins (Cap, prM/M, and Env), and nucleotides 2453 to 10354 encode the non-structural proteins (NS1, NS2A, NS2B, NS3, NS4A, NS4B, and NS5). In particular embodiments, at least one of the introns is inserted between nucleotides 122 to 2452, and at least one intron is inserted between nucleotides 2453 to 10354 of GB Acc. X03700.1.

In embodiments, the flavivirus is a strain of West Nile Virus (WNV) and the nucleotide sequence of the WNV strain is provided at GB Acc. KM659876.1. As shown in Table 1 below, nucleotides 97 to 2469 (of GB Acc. KM659876.1) encode the structural proteins (Cap, prM/M, and Env), and nucleotides 2470 to 10398 encode the non-structural proteins (NS1, NS2A, NS2B, NS3, NS4A, 2K, NS4B, and NS5). In particular embodiments, at least one of the introns is inserted between nucleotides 97 to 2469, and at least one intron is inserted between nucleotides 2470 to 10398 of GB Acc. KM659876.1.

In embodiments, the flavivirus is the Dengue 2 PDK-53 strain and the nucleotide sequence of the Dengue 2 PDK-53 strain is provided at GB Acc. M84728.1. As shown in Table 1 below, nucleotides 100 to 2421 (of GB Acc. M84728.1) encode the structural proteins (Cap, prM/M, and Env), and nucleotides 2422 to 10269 encode the non-structural proteins (NS1, NS2A, NS2B, NS3, NS4A, 2K, NS4B, and NS5). In particular embodiments, at least one of the introns is inserted between nucleotides 100 to 2421, and at least one intron is inserted between nucleotides 2422 to 10269 of GB Acc. M84728.1.

In embodiments, the flavivirus is a strain of Zika virus and the nucleotide sequence of the Zika strain is provided at GB Acc. NC_012532. As shown in Table 1 below, nucleotides 107 to 2476 (of GB Acc. NC_012532) encode the structural proteins (Cap, prM/M, and Env), and nucleotides 2477 to 10363 encode the non-structural proteins (NS1, NS2A, NS2B, NS3, NS4A, 2K, NS4B, and NS5). In particular embodiments, at least one of the introns is inserted between nucleotides 107 to 2476, and at least one intron is inserted between nucleotides 2477 to 10363 of GB Acc. NC_012532.

As another example, the non-structural proteins of an alphavirus include the nsP1, nsP2, nsP3, and nsP4 proteins. The structural proteins of an alphavirus include the capsid (Cap), E3, E2, 6K and E1 proteins. In embodiments, at least one of the introns is inserted in a gene encoding the nsP1, nsP2, nsP3, or nsP4 protein of an alphavirus, and at least one of the introns is inserted in a gene encoding the Cap, E3, E2, 6K, or E1 protein of an alphavirus. For the alphavirus, the non-structural proteins and the structural proteins are each part of a separate polyprotein, such that the non-structural genes together encode a polyprotein and the structural genes together encode a second polyprotein.

In embodiments, the alphavirus is the VEEV TC-83 strain and the nucleotide sequence of the VEEV strain is provided at GB Acc. L01443. As shown in Table 2 below, nucleotides 45 to 7523 (of GB Acc. L01443) encode the non-structural proteins (nsP1, nsP2, nsP3, and nsP4), and nucleotides 7562 to 11326 encode the structural proteins (Cap, E3, E2, 6K, and E1). In other embodiments, at least one of the introns is inserted between nucleotides 45-7523, and at least one intron is inserted between nucleotides 7562 to 11326 of GB Acc. L01443.

In embodiments, the alphavirus is the CHIKV 181/25 strain and the nucleotide sequence of the CHIKV strain is provided at GB Acc. L37661.3. As shown in Table 2 below, nucleotides 50 to 7471 (of GB Acc. L37661.3) encode the non-structural proteins (nsP1, nsP2, nsP3, and nsP4), and nucleotides 7450 to 11283 encode the structural proteins (CAP, E3, E2, 6K, and E1). In other embodiments, at least one of the introns is inserted between nucleotides 50-7471, and at least one intron is inserted between nucleotides 7540 to 11283 of GB Acc. L37661.3.

As a further example, non-structural proteins of a picornavirus include the P2-A, P2-B, P2-C, P3-A, P3-B, P3-C, and P3-D proteins. The structural proteins of a picornavirus include the P1-A, P1-B, P1-C, and P1-D proteins. In embodiments, at least one of the introns is inserted in a gene encoding the P2-A, P2-B, P2-C, P3-A, P3-B, P3-C, or P3-D protein of a picornavirus, and at least one of the introns is inserted in a gene encoding the P1-A, P1-B, P1-C, or P1-D protein of a picornavirus. These structural and non-structural proteins of the picornavirus are part of a polyprotein that is encoded by the structural and non-structural genes of the picornavirus.

In embodiments, the picornavirus is an attenuated human poliovirus 2 strain and the nucleotide sequence of the human poliovirus 2 strain is provided at GB Acc. D00625.1. As shown in Table 3 below, nucleotides 748 to 3384 (of GB Acc. D00625.1) encode the structural proteins (P1-A, P1-B, P1-C, and P1-D), and nucleotides 3385 to 7362 encode the non-structural proteins (P2-A, P2-B, P2-C, P3-A, P3-B, P3-C, and P3-D). In other embodiments, at least one of the introns is inserted between nucleotides 748 to 3384, and at least one intron is inserted between nucleotides 3385 to 7362 of GB Acc. D00625.1.

In embodiments, the (+)SS RNA virus is an attenuated virus or is attenuated (or has enhanced attenuation) through its production via the iDNA technology process. Tables 1, 2, and 3 provide exemplary (+)SS RNA viruses. There exist other examples of (+) SS RNA viruses and also various strains of each type of (+)SS RNA viruses.

TABLE 1

FLAVIVIRUS GENOME COMPOSITION

| | | Structural genes | | | Non-structural genes | | | | | | | | Total genome size (nt)/ polyprotein |
|---|---|---|---|---|---|---|---|---|---|---|---|---|---|
| Virus ID | GenBank # | Capsid | prM/M | Envelope | NS1 | NS2A | NS2B | NS3 | NS4A | 2K | NS4B | NS5 | (total aa) |
| JEV SA14-14-2 | AF315119.1 | 96 to 476 | 477 to 977 | 978 to 2477 | 2478 to 3722 | 3723 to 4214 | 4215 to 4607 | 4608 to 6464 | 6465 to 7265 | | 7266 to 7676 | 7677 to 10391 | 10977 nt 3432 aa |
| YF17D | X03700.1 | 122 to 481 | 482 to 973 | 974 to 2452 | 2453 to 3679 | 3680 to 4180 | 4181 to 4570 | 4571 to 6439 | 6440 to 7300 | | 7301 to 7636 | 7637 to 10354 | 10862 nt 3411 aa |
| WNV | KM659876.1 | 97 to 465 | 466 to 741 742 to 966 | 967 to 2469 | 2470 to 3525 | 3526 to 4218 | 4219 to 4611 | 4612 to 6468 | 6469 to 6834 | 6835 to 6915 | 6916 to 7683 | 7684 to 10398 | 11028 nt 3434 aa |
| Dengue 2 PDK-53 | M84728.1 | 100 to 438 | 439 to 711 712 to 936 | 937 to 2421 | 2422 to 3477 | 3478 to 4131 | 4132 to 4521 | 4522 to 6375 | 6376 to 6825 | | 6826 to 7569 | 7570 to 10269 | 10723 nt 3391 aa |
| Zika virus | NC_012532 | 107 to 472 | 473 to 751 752 to 976 | 977 to 2476 | 2477 to 3532 | 3533 to 4210 | 4211 to 4600 | 4601 to 6451 | 6452 to 6832 | 6833 to 6901 | 6902 to 7654 | 7655 to 10363 | 10794 nt 3419 aa |

TABLE 2

ALPHAVIRUS GENOME COMPOSITION

| Virus ID | GenBank # | Non-structural genes | | | | Structural genes | | | | | Total genome size (nt)/ polyprotein (total aa) |
|---|---|---|---|---|---|---|---|---|---|---|---|
| | | nsP1 | nsP2 | nsP3 | nsP4 | capsid | E3 | E2 | 6K | E1 | |
| VEEV TC-83 | L01443 | 45 to 1649 | 1650 to 4031 | 4032 to 5702 | 5703 to 7523 | 7562 to 8386 | 8387 to 8563 | 8564 to 9832 | 9833 to 10000 | 10001 to 11326 | 11446 nt 2493 aa non-structural polyprotein, 1255 structural polyprotein |
| CHIKV TSI-GSD-218 (181/25) | L37661.3 | 50 to 1654 | 1655 to 4048 | 4049 to 5638 | 5639 to 7471 | 7540 to 8322 | 8323 to 8514 | 8515 to 9783 | 9784 to 9966 | 9967 to 11283 | 12036 nt 2474 aa non-structural polyprotein 1246 aa structural polyprotein |

TABLE 3

PICORNAVIRUS GENOME COMPOSITION

| | | Structural genes (748 to 3384) | | | | Non-structural genes (3385 to 7362) | | | | | | Total genome size (nt)/ polyprotein |
|---|---|---|---|---|---|---|---|---|---|---|---|---|
| Virus ID | GenBank # | P1-A | P1-B | P1-C | P1-D | P2-A | P2-B | P2-C | P3-A | P3-B | P3-C | P3-D | (total aa) |
| Human poliovirus 2 | D00625.1 | 748 to 954 | 955 to 1767 | 1768 to 2481 | 2482 to 3384 | 3385 to 3831 | 3832 to 4122 | 4123 to 5109 | 5110 to 5370 | 5371 to 5436 | 5437 to 5985 | 5986 to 7362 | 7434 nt 2205 aa |

In embodiments, the DNA contained in the vector described herein includes a DNA encoding a (+)SS RNA virus. In other embodiments, the DNA encoding the (+)SS RNA virus is as set forth in GB Acc. AF315119.1, X03700.1, KM659876.1, M84728.1, NC_012532, L01443, L37661.3, or D00625.1 and has been modified to include at least three introns. At least one of the introns is in the DNA region encoding the structural proteins of the (+)SS RNA virus, and at least one of the introns is in the DNA region encoding the non-structural proteins.

In particular embodiments, the DNA contained in the vector described herein is set forth in SEQ ID NO: 1.

In embodiments, the DNA encoding a (+)SS RNA virus contained in the vector hybridizes under very low stringency conditions, low stringency conditions, medium stringency conditions, medium-high stringency conditions, high stringency conditions, or very high stringency conditions with SEQ ID NO: 1 or its complementary strand. In embodiments, the DNA encoding the (+)SS RNA hybridizes at various stringency conditions described herein to the nucleotides at about 1011 to 12320 of SEQ ID NO: 1 or a complementary strand thereof. The stringency conditions are provided in Sambrook et al. (J. Sambrook, E. F. Fritsch, and T. Maniatis, 1989, Molecular Cloning, A Laboratory Manual, 2d edition, Cold Spring Harbor, N.Y.), which is incorporated by reference in its entirety.

In embodiments, the DNA encoding a (+)SS RNA virus contained in the vector hybridizes under very low stringency conditions, low stringency conditions, medium stringency conditions, medium-high stringency conditions, high stringency conditions, or very high stringency conditions with the DNA set forth in in GB Acc. AF315119.1, X03700.1, KM659876.1, M84728.1, NC_012532, L01443, L37661.3, or D00625.1 or a complementary strand thereof and the DNA encoding the (+)SS RNA virus includes at least three introns, one of which is in the DNA region encoding the structural proteins and one of which is in the DNA region encoding the non-structural proteins.

In embodiments, the DNA encoding a (+)SS RNA virus contained in the vector has at least 80%, 85%, 90%, 95%, 96%, 97%, 98%, or 99% sequence identity with SEQ ID NO: 1. For purposes of the present disclosure, the degree of identity between two deoxyribonucleotide sequences is determined using the Needleman-Wunsch algorithm as implemented in the Needle program of the EMBOSS package, preferably version 3.0.0 or later.

In embodiments, the DNA encoding a (+)SS RNA virus contained in the vector has at least 80%, 85%, 90%, 95%, 96%, 97%, 98%, or 99% sequence identity with the DNA set forth in in GB Acc. AF315119.1, X03700.1, KM659876.1, M84728.1, NC_012532, L01443, L37661.3, or D00625.1 and the DNA encoding the (+)SS RNA virus includes at least three introns, one of which is in the DNA region encoding the structural proteins and one of which is in the DNA region encoding the non-structural proteins.

In embodiments, the amino acid sequence of the (+)SS RNA virus encoded by the DNA contained in the vector has at least 80%, 85%, 90%, 95%, 96%, 97%, 98%, or 99% sequence identity with the amino acid sequence set forth in in GB Acc. AF315119.1, X03700.1, KM659876.1. M84728.1. NC_012532, L01443, L37661.3, or D00625.1. The DNA encoding the amino acid sequence of the (+)SS RNA virus includes at least three introns, one of which is in the DNA region encoding the structural proteins and one of which is in the DNA region encoding the non-structural proteins.

The present disclosure also provides methods of preparing large quantities of the DNA described herein. The DNA encoding the RNA molecule can be synthesized chemically and cloned into a desired vector for replication. The methods for preparing large quantities of the DNA include transforming the vector containing the DNA into a host cell and culturing the host cell under conditions to enable replication of large quantities of the vector containing the DNA. The host cells for preparing the DNA include bacterial cells. In embodiments, the bacterial cells include *E. coli*. Other suitable host cells or chemical means for preparing the DNA can also be used.

Additionally, the present disclosure provides a method of improving stability and yield of DNA encoding the genomic RNA of an infectious (+)SS RNA virus in a bacterial host cell, for example *E. coli*. The DNA, specifically the cDNA, of some (+)SS RNA viruses, such as flaviviruses including Yellow fever virus or JEV, are very difficult to propagate as plasmids in *E. coli* because of instability and/or toxicity of plasmids containing cDNA of interest. In the past, to improve yields of plasmid, low-copy plasmids that reduce the toxicity as well as the yield of flavivirus DNA have been used. Moreover, introns have been inserted to improve stability of the plasmid. Two introns have been inserted into a low-copy JEV cDNA plasmid to improve stability of the full length clone (Yamashchikov et al. 2001). However, it is desirable to generate high yields of the plasmid, especially for preparing vaccines.

The present disclosure provides a method which utilizes standard, high copy plasmid to propagate the cDNA encoding a (+)SS RNA virus in bacterial host cells, such as *E. coli*. The method comprises incorporating three or more introns in the cDNA of a (+)SS RNA virus. At least one of the introns is located in a region encoding a structural protein of the (+)SS RNA virus, and at least one of the introns is located in a region encoding a NS protein of the (+)SS RNA virus.

The effectiveness of multiple introns in enhancing stability and enabling high yield is surprising because each intron is supposed to be spliced out individually from the RNA during transcription in order to restore the original sequence encoding the infectious (+)SS RNA virus. Moreover, when there are several introns, for example three or more, the possibility of alternative splicing is increased, in that one intron will splice out with the second or third intron resulting in the deletion of the genes (or nucleotides) between the introns. This process of alterative splicing leads to deletions and results in a non-functional virus. The present disclosure provides a method of producing stable plasmid in bacterial host cells, such as *E. coli*. Any plasmid or viral vector can be used for inserting the cDNA, for example, pcDNA3.1, pBR322, pCI, pUC, pCR, pCR-TOPO, vaccinia vector, AAV vector, adenovirus vector, and other plasmids or vectors known in the art for propagation in bacterial host cells. Software programs and known methods can be employed to predict the optimal promoters for the bacterial host. The plasmid including the cDNA containing at least three introns is characterized by enhanced stability in the bacterial host cell as compared to a control. The yield of the plasmid is also increased as compared to a control plasmid. A control plasmid is a plasmid including a cDNA with less than three introns and encoding a genomic RNA of a (+)SS RNA virus.

The cDNA can also include regulatory elements, for example, a promoter suitable for expression in a eukaryotic host cell, operably linked to the DNA encoding the (+)SS RNA virus.

The present disclosure describes compositions including the vectors described herein and a carrier. The compositions can be pharmaceutical compositions including the vectors and a pharmaceutically acceptable carrier. The compositions can include effective amounts of the vector. The compositions can include therapeutically effective amounts of the vector for preventing and treating diseases. For therapeutic purposes, the DNA contained in the vector encodes the RNA molecule of a nonpathogenic and/or an attenuated virus or chimeric virus. In particular embodiments, the compositions are used as vaccines to protect against diseases caused by (+)SS RNA virus.

The present disclosure describes host cells transfected with the vectors described herein. The host cells can be prokaryotic cells or eukaryotic cells, such as mammalian cells. Prokaryotic cells include *E. coli*. Eukaryotic cells include baby hamster kidney cells (BHK), Vero cell, a CHO cell, or a MDCK.

The present disclosure also describes compositions including viruses obtained from the vectors described herein and a carrier. The compositions described herein include a homogeneous population of clonally purified viruses produced using iDNA® technology. iDNA® technology generates a homogeneous population of viruses. As an example, the population of viruses produced by iDNA® technology contains a higher percentage of viruses having identical nucleotide sequences. In embodiments, the homogeneous population of (+)SS RNA viruses described herein contains at least about 5%, 10%, 15%, 20%, 25%, 30%, 35%, 40%, 45%, or 50% more viruses encoded by identical nucleotide sequences than the population of (+)SS RNA viruses produced by conventional methods. As an example, the homogeneous population of JEV viruses described herein contains at least about 5%, 10%, 15%, 20%, 25%, 30%, 35%, 40%, 45%, or 50% more JEV encoded by SEQ ID NO: 1 than a population of JEV produced by conventional method.

Moreover, the homogeneous population of (+)SS RNA viruses can contain greater than about 50%, 60%, 70%, 80%, 90%, 95%, 99% of a quasispecies of virus.

The compositions can include effective amounts of the virus and a carrier. The compositions can be a pharmaceutical composition and include therapeutically effective amounts of the virus and a pharmaceutically acceptable carrier for treating and preventing diseases. For therapeutic purposes, the homogeneous virus population of the composition includes nonpathogenic, attenuated, or nonpathogenic and attenuated viruses, and can also include live nonpathogenic, live attenuated, or live nonpathogenic and attenuated viruses. In particular embodiments, the compositions including a homogeneous population of clonally purified viruses are used as vaccines to protect against diseases caused by (+)SS RNA virus.

Carriers include a diluent, adjuvant, excipient, or vehicle with which the vector described herein is administered. The composition, if desired, can also contain minor amounts of wetting or emulsifying agents, or pH buffering agents. These compositions can take the form of solutions, suspensions, emulsion, tablets, pills, capsules, powders, sustained-release formulations, combinations thereof and the like.

Pharmaceutically acceptable carrier refers to a vehicle for containing the vector described herein that can be injected into a subject without adverse effects. Pharmaceutically acceptable carriers include sterile liquids, such as water and oils, including those of petroleum, animal, vegetable or synthetic origin, such as peanut oil, soybean oil, mineral oil, sesame oil, combinations thereof and the like. Suitable pharmaceutically acceptable carriers include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, combinations thereof and the like. Other examples of suitable pharmaceutical carriers are described in "Remington's Pharmaceutical Sciences" by E. W. Martin.

The present disclosure also provides methods for preparing a homogeneous population of clonally purified live (+)SS RNA viruses. The method includes transfecting the vector described herein into a eukaryotic host cell, culturing the host cell under conditions to allow production of live (+)SS RNA viruses, and isolating the live (+)SS RNA viruses from the culture medium for growing the host cell to obtain a homogeneous population of clonally purified live (+)SS RNA viruses. Examples of eukaryotic host cells for preparing a homogeneous population of clonally purified live (+)SS RNA viruses include Vero cells, CHO cells, and MDCK cells and other mammalian cells.

In embodiments, the method described immediately above can be used to prepare a pharmaceutical composition including a therapeutically effective amount of a homogeneous population of clonally purified live (+)SS RNA viruses for use as a vaccine for immunizing a subject.

The pharmaceutical compositions described herein can be formulated into vaccines. The vaccines described herein include a properly formulated vector described herein including a DNA encoding a full-length genomic RNA molecule of an infectious nonpathogenic and/or attenuated (+)SS RNA virus operably linked to a promoter suitable for expression in a eukaryotic cell. Such DNA when injected into a subject, will initiate limited replication of attenuated virus and will induce a protective immune response.

The present disclosure describes methods for using the vaccines and compositions described herein to protect subjects from diseases caused by (+)SS RNA viruses. Subjects include humans and veterinary animals (dogs, cats, reptiles, birds, etc.) including livestock (horses, cattle, goats, pigs, chickens, etc.) and research animals (monkeys, rats, mice, fish, etc.). Subjects in need of (in need thereof) are subjects in need of vaccination or immunization from diseases caused by (+)SS RNA viruses. The vaccines described herein can be specifically formulated to protect mammalian subjects, particularly humans, from diseases.

As used herein, the term "protects against a disease" includes prevention and treatment of the disease. The term "treating," "treatment" and the like are used to refer to obtaining a desired pharmacological and/or physiological effect, and refer to a process by which the symptoms of a disease caused by a (+)SS RNA virus is completely eliminated or ameliorated to any clinically and/or quantitatively measurable degree. The term "preventing" refers to a process by which a disease caused by a (+)SS RNA viruses is obstructed and/or delayed. In embodiments, the vaccines described herein protects against a disease caused by a (+)SS RNA virus by inducing an "immune response" which includes a T cell response, increased serum levels of antibodies to an antigen, the presence of neutralizing antibodies to an antigen (such as a (+)SS RNA virus polypeptide), or combinations thereof. The term "protection" or "protective immunity" includes the ability of the serum antibodies or T cell response induced during immunization to protect (partially or totally) against disease or death caused by (+)SS RNA viruses.

The vaccines described herein can be utilized in various ways to protect against diseases caused by (+)SS RNA viruses. The vaccines containing the vector described herein can be administered directly to subjects by various means including electroporation, lipofection, gene gun, microinjection, microparticles, microcapsules, cell fusion, DEAE dextran, calcium phosphate precipitation, or other genetic transfer methods. In the tissues of the subject, the full-length infectious (+)SS RNA is generated by transcription, which initiates production of live attenuated (+)SS RNA viruses in vivo. The (+)SS RNA viruses are released from the cells in vivo in the tissues of the subject, which initiates induction of effective immune response to the vaccine.

Moreover, using the iDNA® technology, the vector can be introduced by electroporation or any other acceptable means known in the art into eukaryotic cells. The live attenuated viruses produced by the introduction of the genetically stable, sequenced DNA vector is a homogenous virus population and contains a lower number of quasispecies thus presenting an advantage over conventional live attenuated vaccines. Accordingly, the homogenous population of live attenuated viruses generated from the vector described herein can be configured into a pharmaceutically acceptable formulation suitable for vaccine administration to subjects.

Administration of the vaccine can be by any route typically used for vaccination, including topical, subcutaneous, intravenous, intramuscular, intradermal, intraperitoneal, oral, inhalation, or combinations thereof.

The vaccines described herein include a therapeutically effective amount of the vector described herein or the homogeneous population of clonally purified (+)SS RNA viruses described herein. A "therapeutically effective amount" is that amount necessary so that the vaccine performs its immunological role without causing overly negative effects in the subject to which the composition is administered. The exact amount to be administered will vary according to factors such as the strength of the transcriptional and translational promoters used, the type of condition being treated, the mode of administration, as well as the other ingredients in the composition. In embodiments, the vaccine includes from about 1 ng to about 1 mg of the vector.

Unlike conventional DNA vaccines, the vaccines described herein can induce effective immunity with a single vaccination, without multiple boosts. Moreover, only a low dose of the vector or of the homogeneous population of clonally purified (+)SS RNA viruses is needed. In embodiments, a low dose of about 1 ng to about 1 µg, about 10 ng to about 1 µg, or about 100 ng to about 1 µg of the vector or of the homogeneous population of viruses could be used. Further, when compared with a conventional DNA vaccine, one could use about 5 fold to about 100 fold less of the vector, about 10 fold to about 100 fold less of the vector, about 25 fold to about 100 fold less of the vector, or about 50 fold to about 100 fold less of the vector or the population of viruses.

In embodiments, the immunogenicity of DNA vaccines can be modified by formulating with one or more pharmaceutically acceptable adjuvants or immunostimulants, such as alpha-interferon, beta-interferon, gamma-interferon, granulocyte macrophage colony stimulator factor ("GM-CSF"), macrophage colony stimulator factor ("M-CSF"), interleukin 2 ("IL-2"), interleukin 12 ("IL-12"), and CpG oligonucleotides. For preparing such compositions, methods well known in the art can be used. In certain embodiments, the DNA is generated in *E. coli* cells as a vector, containing unmethylated CpG motifs and itself constitutes an immunostimulating molecule that activates the immune system via toll-like receptors.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As an example, lack of a material effect is evidenced by lack of a statistically-significant protection against a viral infection by the vaccines described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") described herein is intended merely to better illuminate the invention and does not pose a limitation on the scope of the invention otherwise claimed. No language in the specification should be construed as indicating any non-claimed element essential to the practice of the invention.

The following examples illustrate exemplary embodiments and methods. They are not intended, nor are they to be construed, as limiting the scope of the disclosure. It will be clear that the methods can be practiced otherwise than as particularly described herein. Numerous modifications and variations are possible in view of the teachings herein and, therefore, are within the scope of the disclosure.

Exemplary Embodiments

1. A vector comprising a DNA encoding a RNA molecule operably linked to a promoter suitable for expression of the vector or DNA in a eukaryotic cell, wherein the RNA molecule encodes an infectious positive single stranded ((+)SS) RNA virus, and wherein the DNA comprises at least three introns.
2. The vector of embodiment 1, wherein the (+)SS RNA virus is a flavivirus, alphavirus, picornavirus, rubivirus, coronavirus, Norwalk virus, Hepatitis A virus, Hepatitis C virus, severe acute respiratory (SAR) virus, and lentivirus.
3. The vector of embodiment 1 or 2, wherein the flavivirus is a Japanese encephalitis virus (JEV), Dengue virus, Yellow Fever virus, West Nile virus, tick borne encephalitis virus, Hepatitis C virus, and Zika virus.
4. The vector of any one of embodiments 1-3, wherein the flavivirus is JEV.
5. A vector comprising a DNA encoding a chimeric RNA molecule operably linked to a promoter suitable for expression of the vector or DNA in a eukaryotic cell, wherein the chimeric RNA molecule encodes an infectious (+)SS RNA virus, and wherein the DNA comprises at least three introns.
6. The vector of embodiment 5, wherein the (+)SS RNA virus is encoded by a chimeric RNA molecule comprising the RNA of at least two different (+)SS RNA viruses.
7. The vector of embodiments 5 or 6, wherein the at least two different (+)SS RNA viruses comprises JEV and at least one other virus, Yellow fever virus and at least one other virus, and Dengue virus and at least one other virus.
8. The vector of any one of embodiments 4-7, wherein the at least one other virus is a Zika virus, a West Nile virus, a Yellow fever virus, or a Dengue virus.
9. The vector of any one of embodiments 4-8, wherein the at least two (+)SS RNA viruses are a JEV and a Zika virus.
10. The vector of any one of embodiments 1-9, wherein at least one intron is in a region encoding a non-structural protein and one intron is in a region encoding a structural protein.
11. The vector of any one of embodiments 1-10, wherein the intron contains a stop codon or several stop codons.
12. The vector of any one of embodiments 1-11, wherein the DNA comprises three introns.
13. The vector of any one of embodiments 1-12, wherein the DNA comprises at least four introns, at least five introns, or at least six introns.
14. The vector of claim any one of embodiments 1-13, wherein the infectious (+) SS RNA virus is a nonpathogenic virus.
15. The vector of any one of embodiments 1-14, wherein the nonpathogenic virus is an attenuated virus.
16. The vector of any one of embodiments 1-15, wherein the promoter is a CMV promoter, a RSV promoter, a SV40 promoter, a HSV promoter, a human Pol I promoter, a human Pol II promoter, or a human Pol III promoter.
17. The vector of any one of embodiments 1-16, wherein the promoter is located at about 12 to 18 nucleotides upstream of a transcription start site.
18. The vector of any one of embodiments 1-17, wherein the promoter is located at about 15 nucleotides upstream of a transcription start site.
19. A composition comprising the vector of any one of embodiments 1-18 and a carrier.
20. A pharmaceutical composition comprising the vector of any one of embodiments 1-20 and a pharmaceutically acceptable carrier.
21. A vaccine comprising a therapeutically effective amount of a vector described in any one of embodiments 1-20.
22. A vaccine comprising a therapeutically effective amount of a pharmaceutical composition including a vector described in any one of the embodiments 1-21.
23. A homogenous population of clonally purified (+)SS RNA virus obtained from eukaryotic cells transfected with the vector described in any one of embodiments 1-23.
24. A composition comprising the homogeneous population of clonally purified (+)SS RNA virus of embodiment 23 and a carrier.
25. A pharmaceutical composition comprising the homogenous population of clonally purified (+) SS RNA virus of embodiments 23 or 24 and a pharmaceutically acceptable carrier.
26. A vaccine comprising a therapeutically effective amount of a homogeneous clonally purified live (+)SS RNA virus population obtained from cells transfected with the vector described in any one of embodiments 1-25.
27. A method of preparing a homogeneous clonally purified live (+)SS RNA virus population, wherein the method comprises transfecting the vector described in any one of embodiments 1-26 into a eukaryotic cell and isolating (+)SS RNA viruses, thereby obtaining the homogeneous clonally purified live (+)SS RNA virus population.
28. The method of any one of embodiments 1-27, wherein the eukaryotic cell is a Vero cell, a CHO cell, or a MDCK cell.
29. A method of preparing a vaccine for protecting a subject against a disease caused by an infectious (+)SS RNA virus, wherein the method comprises transfecting the vector of any one of embodiments 1-29 into a eukaryotic cell, culturing the transfected eukaryotic cells, and isolating the (+)SS RNA viruses, thereby obtaining a vaccine.
30. The method of any one of embodiments 1-29, wherein the eukaryotic cell is a Vero cell, a CHO cell, or a MDCK cell.
31. A method for protecting a subject against a disease caused by an infectious (+)SS RNA virus, wherein the method comprises administering the vaccine of any one of embodiments 1-30 to a subject.
32. The method of any one of embodiments 1-31, wherein the subject is a mammal.
33. The method of any one of embodiments 1-32, wherein the mammal is a human or a veterinary animal
34. A method of preparing a stable plasmid comprising a DNA encoding a genomic RNA of an infectious (+)SS RNA virus, wherein the method comprises introducing at least three introns into the DNA, and wherein at least one intron is in the region encoding a structural protein of the (+) SS RNA virus and at least one intron is in the region encoding a non-structural protein of the (+)SS RNA virus.
35. A method of preparing a vector described in any one of embodiments 1-34, wherein the method includes transfecting a vector described in any one of embodiments 1-34 into a host cell and isolating the vector from the host cell.
36. An isolated cell transfected with a vector described in any one of embodiments 1-34.
37. A method of protecting a subject against a disease caused by an infectious (+) SS RNA virus, wherein the method comprises administering a vaccine comprising the homogeneous clonally purified live (+)SS RNA virus population described in any one of embodiments 1-36.

EXAMPLES

Introduction. Japanese encephalitis virus (JEV) is a (+)SS RNA virus. It is the main cause of acute viral encephalitis in the Asia-Pacific region, primarily affecting children and young adults. JEV causes epidemics throughout Asia and is transmitted by the mosquito *Culex tritaeniorhynchus*. Four types of JEV vaccine have been licensed in different regions of the world (CDC, 2016; WHO, 2015). For the past decades, killed virus vaccines were prepared in tissue culture or in mouse brain and have been used to immunize travelers and residents of enzootic countries. Concerns associated with cost, efficacy and safety characteristics of these vaccines have led to the development of alternative vaccines including live-attenuated vaccine SA14-14-2, chimeric vaccine YF-JEV, as well as purified inactivated, tissue culture-derived vaccine (Halstead and Thomas, 2011). Currently, attenuated strain SA14-14-2 derived from its wild-type parental strain SA14 is the most common strain used in vaccine development and production. However, despite available clinical and experimental JEV vaccines, improvements are needed for JEV vaccination due to limitations of currently available vaccines. Among experimental approaches, plasmid DNA vaccines have been developed that expressed structural or non-structural JEV proteins. In a mouse model, DNA vaccines elicited detectable protection against challenge with a lethal dose of JEV (Putnak et al., 2003).

Recently, DNA-launched live-attenuated vaccines have been described, which combine chemical and genetic stability of DNA vaccines with the efficacy of traditional live-attenuated vaccines (Pushko et al., 2016; Tretyakova et al., 2014a; Tretyakova et al., 2013; Tretyakova et al., 2014b). This platform is based on the infectious clone technology and represents plasmid DNA that can launch live-attenuated virus in vitro or in vivo (Jiang et al., 2015; Lukashevich, 2014; Tretyakova et al., 2014a; Tretyakova et al., 2013; Tretyakova et al., 2014b). DNA-launched live-attenuated vaccines were sometimes called iDNA® vaccines in order to distinguish them from the standard DNA vaccines (Pushko et al., 2016; Tretyakova et al., 2014a; Tretyakova et al., 2013; Tretyakova et al., 2014b). In the previous studies, the full-length JEV infectious clone has been made and used to prepare a DNA-launched virus in vitro, and JEV replication was studied in cell culture. Replication of DNA-launched JEV flavivirus in vitro has been confirmed (Mishin et al., 2001; Yamshchikov et al., 2001). However, DNA-launched live-attenuated JEV vaccine has not yet been evaluated in vivo. One potential reason for that was the difficulty of generating stable full-length JEV clone. To improve stability of the plasmid, two introns have been inserted into the low-copy JEV cDNA plasmid to improve stability of the full-length clone (Yamshchikov et al., 2001).

In the current study, DNA-launched live-attenuated JEV vaccine was prepared based on the published sequence of SA14-14-2 vaccine. Plasmid was prepared by using fully synthetic cDNA of SA14-14-2 strain. The yields of the full-length plasmid production in *E. coli* were improved by inserting three synthetic introns in both the structural and non-structural genes of JEV cDNA. The vaccine plasmid was initially confirmed for launching the JEV vaccine in vitro. Furthermore, this novel iDNA® vaccine was evaluated in BALB/c mice for immunogenicity and induction of virus-neutralizing response. Neutralizing antibody was detected after a single dose vaccination with either 500 ng or 5 µg of plasmid suggesting that DNA-launched live attenuated vaccine approach can be utilized for the development of novel JEV vaccine.

Materials and Methods

Cell Lines and Viruses:
African green monkey (Vero) and Baby hamster kidney (BHK) cell lines were obtained from the American Type Culture Collection (ATCC, Manassas, Va.) and were maintained in a humidified incubator at 37° C. and 5% $CO_2$ in αMEM medium supplemented with 10% fetal bovine serum (FBS) and gentamicin sulfate (10 µg/ml) (Thermo Scientific (Thermo), Carlsbad, Calif.).

Plasmids and Preparation of iDNA®:
The full-length nucleotide sequence of cDNA for JEV live attenuated vaccine strain SA14-14-2 (Genbank accession number AF315119.1) was prepared using synthetic biology techniques (Wimmer et al., 2009). The resulting complete JEV cDNA sequence was cloned into kanamycin resistant, high-copy pUC57 plasmid (Genscript, Piscataway, N.J.) carrying pMB1 origin of replication. Any other standard plasmid or viral vector can be used for inserting cDNA, for example, pcDNA3.1, pBR322, pCI, pUC, pCR, pCR-TOPO, vaccinia vector, AAV vector, adenovirus vector and other plasmids or vectors known in the art. CMV major immediate-early promoter was inserted upstream from the full-length SA14-14-2 cDNA. In addition, three synthetic introns have been inserted into the JEV sequence downstream from predicted bacterial promoters with the purpose of preventing synthesis of potentially toxic proteins in *E. coli*. The *E. coli* promoters have been predicted by using BPROM software (SoftBerry, Mount Kisco, N.Y.) to identify sites for intron insertions. Other software or methods can also be utilized to predict promoters. Three chimeric introns were inserted into capsid, envelope, and NS1 genes of SA14-14-2 cDNA by using standard molecular biology methods. Intron sequences were derived from mouse immunoglobulin H chain V-region precursor gene (Genbank accession M12880), or other sources of intron sequences. As a result, plasmid pMG8009 was generated that encoded the SA14-14-2 full-length genomic RNA under transcriptional control of the CMV promoter (FIG. 1). The plasmid was isolated from *E. coli* strain Stbl3 (Thermo), confirmed by DNA sequencing, quantitated, and stored at −20° C.

Transfections and Assays In Vitro:
Vero cells were transfected by electroporation with pMG8009 or control plasmid DNA at concentrations ranging from 10 ng to 1 µg. Transfection was carried out essentially as described previously (Messer et al., 2012; Tretyakova et al., 2013). Production of virus and expression of SA14-14-2 antigens in the transfected Vero cells were determined by the infectious center assay (ICA), indirect immunofluorescence assay (IFA) and western blot. The secreted JEV vaccine virus in the growth medium from transfected Vero cells was detected by standard plaque assay in BHK cells.

Infectious center assay (ICA) was done using Vero cells transfected with pMG8009 or infected with live virus. Vero cells were diluted 10-fold in complete αMEM containing 10% FBS, allowed to adhere for 4 h in in 6-well plates, and covered with 1% agarose overlay. Plates were incubated at 37° C. in 5% $CO_2$ for 3 days to form plaques, which were visualized using staining with neutral red.

For indirect immunofluorescence assay (IFA), pMG8009 DNA-transfected Vero cells were seeded in 8-well chamber slides in complete αMEM. At 48 h posttransfection, cells were rinsed with PBS, dried and fixed with cold acetone, and IFA was carried out using JEV-specific mouse antiserum VR-1259AF (ATCC), followed by the secondary fluorescein-labeled antibody to mouse IgG (H+L) (Kirkegaard and Perry, Gaithersburg, Md.) as described previously (Pushko et al., 2001; Tretyakova et al., 2014b). Mounting medium containing propidium iodide counterstain (Vector Labs, Burlingame, Calif.) has been used to visualize nuclei of the cells.

SDS-PAGE and western blot were used to detect JEV antigens in Vero cells transfected with iDNA®. Transfected Vero cells were harvested on day 9 post transfection, solubilized in the SDS-PAGE sample buffer containing 2-Mercaptoethanol, and proteins were separated by 4-12% SDS-PAGE. Proteins were transferred to nitrocellulose membranes and probed with VR-1259AF JEV-specific antiserum followed by alkaline conjugated secondary antibody and staining using 1-component BCIP/NBT phosphatase substrate (KPL, Gaithersburg, Md.).

Finally, the virus presence in the growth medium was confirmed by standard plaque assay in BHK cells. For virus growth curves, samples were taken at 24 h time intervals. Average and standard deviation values were determined. Each experiment was conducted at least two times to ensure reproducibility.

The virus from transfected cells was harvested at 9 days post infection. After harvest, the vaccine virus was clarified by centrifugation at 3000×g for 10 min and frozen at −80° C.

Immunizations and Serology:

The iDNA® plasmid was isolated from *E. coli* and formulated in phosphate-buffered saline (PBS) to a final concentration of 0.4 mg/ml. Four-week-old female BALB/c mice were anesthetized with isoflurane and vaccinated intramuscularly (i.m.) with a dose of 5 µg or 500 ng of pMG8009 iDNA® vaccine in 50 µl into the medial thighs, tibialis anterior muscle (Noble Life Sciences, Woodbine, Md.). After injection of iDNA®, animals were electroporated as described elsewhere (Tretyakova et al., 2013). For transfection in vivo, various methods can be used including ballistic DNA delivery (Gene gun or similar), chemical transfection using in vivo transfection reagents (PEI, liposomes, or similar), electroporation devices (using BTX (Gentronics), TriGrid (Ichor Medical Systems, Inc., San Diego, Calif.), Inovio or other electrodes or instruments accepted in the field. As a control, the plasmids expressing unrelated gene were injected-electroporated similarly. After vaccinations, animals were observed daily for clinical signs of infection. Sera were collected on days 3 and 4 for viremia detection, and at day 21 (Experiment 1) and 28 (Experiment 2) for antibody response evaluation. For viremia detection, sera were tested individually in direct plaque assay. Alternatively, in order to amplify the virus in the serum, each serum was incubated with Vero cells for 10 days before harvesting. At the time of harvest, Vero cells were observed for cytopathic effects (CPE), while harvested media were tested by plaque assay.

To determine antibody responses, plaque reduction neutralization test (PRNT), western blot, and IFA were performed. For PRNT, an equal volume (0.1 ml) of virus suspension containing 500 PFU/ml and serial twofold dilutions of heat-inactivated serum were incubated 1 h at 37° C., and the serum-virus mixture was plated onto BHK cell monolayers in 12-well plates. An agarose overlay of in αMEM was added and plates were incubated at 37° C. for 3 days prior to neutral red staining and plaque count determination. The endpoint $PRNT_{50}$ titers were expressed as the highest dilution of serum that reduces plaques by 50% as compared to the wells without serum.

For determination of antibody response by IFA, Vero cell monolayers were initially infected with $10^2$ PFU/well of JEV vaccine virus in chamber slides for 24 h in complete αMEM. Then, infected Vero cells were fixed with acetone and used as immobilized antigen essentially as described above. The JEV-infected Vero cell monolayers were probed with sera from vaccinated experimental mice to detect JEV-specific antibodies in the sera. As controls, sera from unvaccinated mice were used.

Example 1: Design and Preparation of DNA-Launched JEV Vaccine

JEV pMG8009 iDNA® vaccine was prepared by inserting CMV major immediate-early promoter upstream from the full-length synthetic JEV cDNA in the pUC57 plasmid. As a result, the pMG8009 plasmid contained the full-length cDNA copy of JEV strain SA-14-14-2 genomic RNA downstream from the CMV promoter. The pUC family has mutations from the pMB1 sequence, which lead to a 20-35 times increase in copy number, with approximately 500 copies per cell (Wu and Liu, 2010). Because the authentic 5' terminus of RNA is important for flavivirus replication (Khromykh et al., 2001), the distance between the CMV promoter and the 5' of JEV cDNA has been optimized to ensure transcription of the functional 5' terminus of the JEV genomic RNA. Ribozyme was included downstream from the 3' end of JEV sequence. According to the previous study (Yamshchikov et al., 2001), insertion of two introns into capsid and E genes improves stability of the cDNA clone, therefore two introns were initially inserted into capsid and E genes, similarly to the methods reported previously (Yamshchikov et al., 2001). However, the resulting full-length JEV cDNA showed low plasmid production yields in the context of pUC57 backbone in *E. coli* strain DH5α as well as in strain Stbl3 and DNA could not be isolated in sufficient quantities. It has been hypothesized that similarly to other flaviviruses, JEV cDNA contains cryptic bacterial promoters that drive synthesis of toxic proteins thus affecting genetic stability and DNA yields in *E. coli* (Rice et al., 1989; Tretyakova et al., 2014b; Yamshchikov et al., 2001). In an attempt to improve genetic stability and increase plasmid production, the third intron sequence was inserted in the full-length JEV cDNA. The site for intron insertion was chosen by mutagenesis and predicting bacterial promoters within JEV sequence. Several putative bacterial promoters within NS1 have been identified. Therefore, an additional synthetic intron was introduced into the JEV NS1 gene resulting in the plasmid pMG8009 containing the full-length cDNA with three introns in the capsid, E, and NS1 genes of JEV SA-14-14-2 cDNA (FIG. 1A). The plasmid pMG8009 was isolated from *E. coli* Stbl3 cells. The resulting pMG8009-JEV was confirmed by DNA sequencing.

Example 2: Characterization of pMG8009 in *E. coli*

Figure 1B:
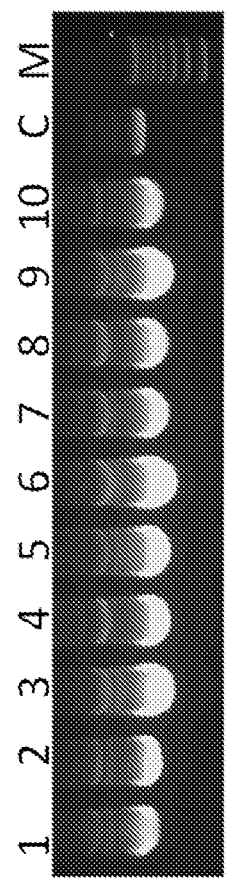

The plasmid pMG8009 was evaluated in *E. coli* for growth and DNA yields. In one experiment, pMG8009 was transformed into chemically competent *E. coli* Stbl3 cells and DNA yields were examined from ten random colonies (FIG. 1B). The plasmid DNA yields, size and appearance were comparable between the isolates and similar to the parent plasmid suggesting uniformity and genetic stability of pMG8009. The pMG8009 yield from Stbl3 cells were approximately 0.5 mg/ml (FIG. 1B). The pMG8009 iDNA® plasmid was isolated from *E. coli* Stbl3 cells resulting in a sterile, endotoxin-free DNA with 95% supercoiled fraction and an A260/A280 ratio of ~1.8.

Example 3: Replication of JEV Vaccine Virus from iDNA® In Vitro

Figure 2B:
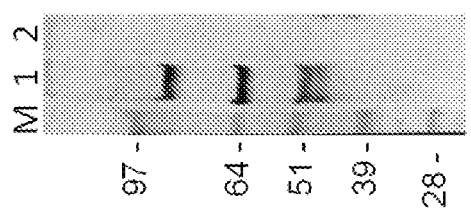
FIGS. 2A-2C show expression of JEV virus in Vero cells transfected with pMG8009 iDNA® plasmid. (a) Infectious center assay (ICA) in Vero cells transfected by electroporation with 1 µg of pMG8009 iDNA® plasmid. (b) Western blot using mouse anti-JEV (ATCC VR-1259AF) antibody. Lane M shows SeeBlue Plus 2 protein molecular weight marker (Thermo). Lane 1 shows JEV antigens in pMG8009-transfected Vero cell. Lane 2, untransfected Vero cells. (c) Indirect IFA using anti-JEV mouse ATCC VR-1259AF. Panels 1, 2, 3 show pMG8009-transfected Vero cells at 170× magnification, untransfected Vero cells (170× magnification), and transfected Vero cells at 400× magnification, respectively.
Figure 2A:
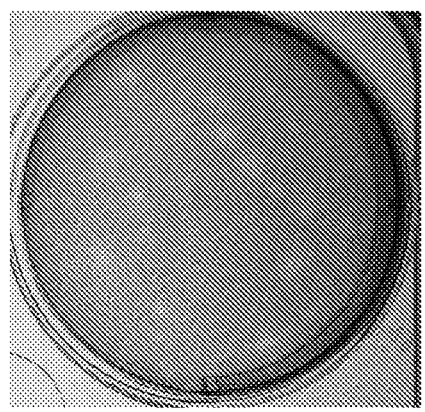
Figure 2C:
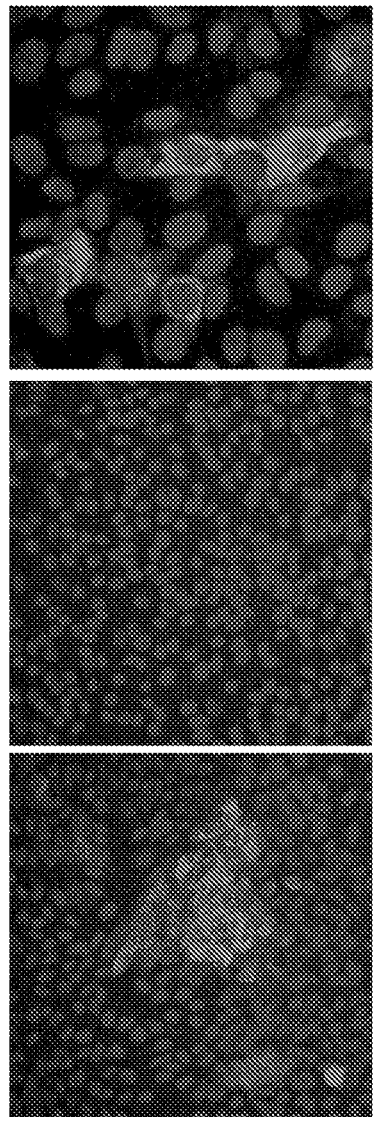

In order to launch replication of live JEV vaccine virus in vitro, Vero cells were transfected with pMG8009 plasmid by electroporation. The transfected Vero cells were analyzed for expression of JEV vaccine virus by ICA, IFA, western blot, while medium from transfected cells was tested by plaque assay. For ICA, a suspension of electroporated Vero cells was seeded into 6-well plates and overlaid with 1% agarose. At 72 h, plaques were detected, indicating replication of virus from the infectious centers, IC (FIG. 2). Specific infectivity of pMG8009-JEV was calculated at ~$10^3$ IC/µg. Expression of JEV antigens in transfected cells was further examined by SDS-PAGE and western blot. The antigen bands were detected in iDNA®-transfected Vero cells (FIG. 2B, lane 1). Western blot confirmed the presence of JEV antigens that were consistent with molecular weights of E, NS1, and prM proteins. As expected, no bands were detected in the uninfected Vero cells (FIG. 2B, lane 2). Furthermore, expression of JEV antigens in transfected cells was confirmed at 24 h posttransfection by IFA using mouse anti-JEV antiserum (FIG. 2C). Foci of JEV positive cells were detected (FIG. 2c, panel 1), while no positive cells or foci were detected in the untransfected Vero control (FIG. 2c, panel 2). As expected for a flavivirus, expression of JEV antigen was found in the cytoplasm of transfected cells (FIG. 2C, panels 1 and 3).

The growth medium from iDNA®-transfected Vero cells was examined for the presence of replicating virus by plaque assay (FIG. 3). Escalating doses of pMG8009 iDNA® were evaluated for the ability to launch live JEV in vitro. Vero cells were transfected with pMG8009 plasmid with doses ranging from 10 ng to 1 µg. As positive control, Vero cells (either electroporated or non-treated) were infected with 1000 PFU JEV. Negative controls were treated with PBS. As expected, no replicating virus was detected in the PBS treated Vero cells (data not shown). Plaques were detected in the supernatant samples of Vero cells transfected with various amounts (10-1000 ng) of iDNA® plasmid or infected with $10^3$ PFU of JEV virus suggesting that iDNA® plasmid has launched replication of live vaccine viruses and that insertion of introns did not affect the ability of pMG8009 to initiate replication of live JEV vaccine virus (FIG. 3A). It is plausible to suggest that iDNA®-launched SA-14-14-2 vaccine will have a greater genetic stability as compared to the classic live attenuated virus SA-14-14-2. Growth curves of viruses from the transfected/infected cells are shown on FIG. 3B. The peak virus titers were similar at all DNA doses tested. In the culture media from cells transfected with 1 µg of pMG8009, the peak titers reached $10^6$-$10^7$ PFU/ml on day 6 posttransfection, similarly to the cells infected with 1000 PFU of JEV. This experiment suggests the equivalency of 1 µg of DNA to 1000 PFU of virus in terms of virus replication kinetics. However, the DNA dose dependence was detectable as a delayed onset of replication when 10 ng or 100 ng of DNA was used. Approximately 48-72 h delay for peak titers was observed when Vero cells were transfected with 10 ng or 100 ng of pMG8009. As shown in FIG. 3B, transfection of only 10 ng of DNA resulted in the replication of JEV virus, with peak virus titers reaching approximately $10^6$-$10^7$ PFU/ml on day 9, with peak titer similar to that from transfections with higher quantities of DNA (FIG. 3B).

These results suggest that the minimal dose of iDNA® to launch JEV vaccine virus in Vero cells is below 10 ng (FIG. 3B), which is consistent with our previous findings with iDNA® plasmids encoding YF flavivirus (Tretyakova et al., 2014b) and VEEV and CHIKV alphaviruses (Tretyakova et al., 2014a; Tretyakova et al., 2013).

Example 4: Immunogenicity of JEV iDNA® Vaccine in BALB/c Mice

Figure 4:
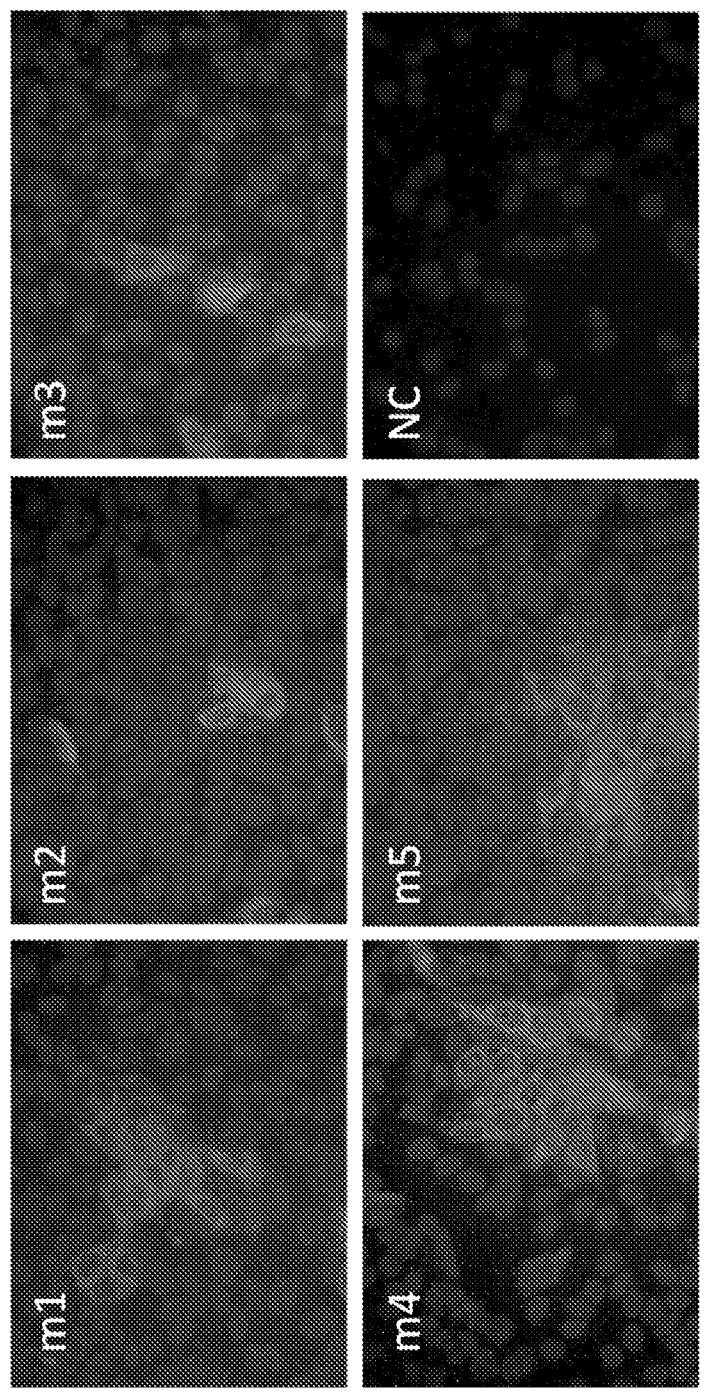
FIG. 4 show Immunogenicity of pMG8009 JEV vaccine in BALB/c mice, by IFA. Mice were vaccinated on day 0 with 5 µg pf pMG8009 plasmid intramuscularly using electroporation. To detect antibodies mice were bled on day 21. Serum from vaccinated mice was used to probe JEV-infected Vero cells in IFA in chamber slides at 1:10 dilution. After incubation with mouse sera, Vero cells were treated with fluorescein-labeled antibodies to mouse IgG (H+L) to visualize cells expressing JEV antigens. Slides were covered with mounting medium containing propidium iodide nuclear counterstain and observed under microscope.

To determine if pMG8009 iDNA® plasmid is immunogenic in vivo, BALB/c mice were vaccinated by injection-electroporation with a single dose of pMG8009 plasmid. JEV vaccines are based on induction of antibodies, and a neutralization titer of 1:10 is considered protective (Plotkin, 2010). Therefore, the focus was on detecting serum antibody response including neutralizing antibodies. Mice were vaccinated with a single i.m. injection of either 500 ng or 5 µg of iDNA® followed by electroporation. As a control, mice were vaccinated by injection with unrelated DNA expressing unrelated gene. After vaccinations, all mice remained healthy with no detectable pathology at the site of injection or adverse effects due to vaccinations. No viremia was detected on days 3 and 4 in the vaccinated mice either by direct plaque assay, or after attempting virus amplification by incubating each serum with Vero cells for 10 days followed by CPE analysis and plaque assays (Table 4). This result indicates no significant presence of replicating vaccine virus on days 3 and 4 after iDNA® injection. In order to detect serum antibodies, IFA and PRNT methods were used. For IFA, Vero cells were initially infected with 100 PFU of SA-14-414-2 virus in chamber slides, fixed, and then probed with immunized mouse sera at 1:10 dilution (FIG. 4). By IFA, all experimental mice vaccinated with 5 µg of pMG8009 have seroconverted as shown in FIG. 4 and Table I.

TABLE 4

Viremia and serum antibodies in mice vaccinated with pMG8009 DNA vaccine.

| | Viremia, PFU/ml* | | Serum Antibody** | |
| --- | --- | --- | --- | --- |
| Dose | Plaque assay | Amplification | IFA | PRNT$_{50}$ |
| 500 ng | <50 (5/5) | <50 (5/5) | +(5/5) | 1:10 (2/5) |
| | | | | 1:20 (2/5) |
| | | | | 1:40 (1/5) |
| 5 µg | <50 (5/5) | <50 (5/5) | +(5/5) | <1:10 (1/5) |
| | | | | 1:10 (3/5) |
| | | | | 1:40 (1/5) |

*For viremia, serum was taken on days 3 and 4. Number of tested/total mice is shown in parentheses.
**For antibody, serum was taken on days 21 and 28. In IFA, "+" indicates positive reaction. In PRNT$_{50}$, dilution of serum that produced 50% reduction of plaques is indicated. Ratio of tested/total mice is shown in parentheses.

Seroconvertion was also detected by indirect fluorescence antibody (IFA) in all mice vaccinated with 500 ng of pMG8009 (Table I). Although IFA is not a quantitative method, increased fluorescence intensity was observed in the sera from mice vaccinated with 5 µg dose as compared to 500 ng group (data not shown). Neutralizing antibodies were also detected by PRNT in the serum of pMG8009 vaccinated mice (Table 4). In the 5 µg vaccination group, most mice had PRNT$_{50}$ titer of 10, which is similar to a protective titer against JEV as described previously (Plotkin, 2010), while one mouse had the titer 40 and one mouse had undetectable titer. In the 500 ng vaccination group, all mice had PRNT$_{50}$ titers in the range from 10 to 40.

Example 5: JEV iDNA® Protects Against JEV Infection

It is known that AG129 mice lacking an intact IFN response are susceptible to virulent DENVs and WNV, and VEEV and YFV vaccine strains, as well as to JEV vaccine strain SA14-14-2 virus. Interferon-deficient AG129 mice are vaccinated with JEV iDNA® plasmid as described above or similarly. As a control, mice receive injection of PBS. JEV live-attenuated vaccine SA14-14-2 is injected intraperitoneally (i.p.) as an infectious challenge virus. Morbidity or mortality is observed and recorded to determine protective effects of iDNA® vaccination. Protection against challenge is observed in vaccinated mice, while no protection is observed in unvaccinated mice.

Example 6: Veterinary Vaccination

Pigs are vaccinated with JEV iDNA® plasmid as described above or similarly. As a control, pigs are injected with PBS. Wild-type virulent JEV virus is injected as an infectious challenge virus. Morbidity or mortality is observed in pigs to determine protective effects of iDNA® vaccination. Protection against challenge is observed in vaccinated pigs, while no protection is observed in unvaccinated animals.

CONCLUSION

JEV is a member of Flavivirus family and a cause of Japanese encephalitis, a zoonotic disease transmitted by mosquitoes and amplified in pigs. Endemic JEV transmission has been reported in humans in 24 countries in the South-East Asia and Western Pacific, exposing more than 3 billion people to risks of JEV infection (WHO, 2015). There is no specific treatment for the disease and current therapeutic approaches are focused on support for the patient to overcome the infection. However, prophylactic vaccines are available worldwide. There are 4 main types of JEV vaccines including inactivated mouse brain-derived vaccines, inactivated Vero cell-derived vaccines, live attenuated vaccines, and live recombinant vaccines (WHO, 2015). Over the past years, the live attenuated SA14-14-2 vaccine manufactured in China has become the most widely used vaccine in endemic countries. Cell-culture based inactivated vaccines and the live recombinant vaccine based on the Yellow fever vaccine strain have also been approved and WHO-prequalified. In the U.S., vaccination is recommended for travelers who plan to spend a month or more in endemic areas during JEV transmission season. Inactivated Vero cell culture-derived IXIARO vaccine is the only vaccine approved in the U.S. (CDC, 2016), which is given as two doses spaced 28 days apart. Veterinary vaccination against JEV has also been conducted, with live attenuated and inactivated vaccines available for swine (Lutticken et al., 2007).

Previous results suggested that both live and inactivated JEV vaccines are safe and effective against JEV and can also elicit strong cross-immunity and protection against Dengue, a related flavivirus (Li et al., 2016). However, there was also an indication of JEV vaccine-facilitated Dengue virus infection-enhancement antibody in adults (Saito et al., 2016). Therefore, additional research is needed, and despite existing vaccines, improvements may be needed for JEV vaccination due to limitations of current vaccines.

DNA vaccines for JEV have been studied as alternative to traditional vaccines due to their potential to be safe and inexpensive formulations. Experimental DNA vaccines have been developed using plasmids, which expressed JEV proteins (Putnak et al., 2003). Plasmids expressing the E protein induced JEV neutralizing antibodies, which are important indicators of protection (Konishi et al., 1999). Plasmid DNA vaccine encoding prM and E proteins appeared to provide more effective vaccination as compared with a construct expressing E protein alone (Konishi et al., 2003; Wu et al., 2006). However, similarly to other standard DNA vaccines, the immunogenicity of plasmid DNA encoding of JEV proteins was relatively low as compared to inactivated vaccine (Bharati et al., 2005; Kaur et al., 2002). The immune response could be augmented by using advanced adjuvants and electroporation. DNA vaccine expressing prM-E proteins of JEV was found effective in mice following i.m. injection; however, when accompanied with electroporation, immune responses were improved in mouse and pig models (Sheng et al., 2016). The use of granulocyte-macrophage colony-stimulating factor to enhance immunogenicity of prM-E DNA based vaccine has been reported (Zhai et al., 2015).

DNA-launched live attenuated vaccines was configured to prepare novel experimental DNA-based vaccine for JEV. In the pMG8009, the full-length synthetic cDNA of SA-14-14-2 strain was introduced downstream from the CMV promoter, which resulted in the transcription of the "infectious" genomic viral RNA and launching the vaccine virus in eukaryotic cells. The advantages of DNA-launched iDNA® vaccines include the genetic and physical stability, ease of production, and high purity of the DNA vaccines, as well as high efficacy of live attenuated vaccines (Pushko et al., 2016). Traditional cell substrates used for vaccine production are often contaminated with latent viruses that can be identified by next generation (NGS) sequencing and other methods (Onions et al., 2011). In contrast, endotoxin-free DNA can be isolated without latent viruses or impurities associated with cell culture production. However, preparation of the full-length flavivirus cDNA has been notoriously difficult due to the instability in E. coli (Rice et al., 1989; Tretyakova et al., 2014b; Tsetsarkin et al., 2016; Yamshchikov et al., 2001). The challenge of preparing full-length JEV cDNA clone in E. coli was solved in the current study by insertion of three distinct synthetic intron sequences in the structural and non-structural JEV genes. In the previous study, two introns were inserted into the JEV structural genes, which facilitated preparation of the full-length clone (Yamshchikov et al., 2001). It was found that inclusion of the third intron in the non-structural genes in addition to two introns in the structural genes considerably improved cDNA preparation, as well as the yields of the pUC backbone with kanamycin resistance. Furthermore, in the first proof-of-concept studies in vivo, it was demonstrated that a single dose of 500 ng or 5 µg of pMG8009 plasmid induced immune response to JEV in mice including JEV neutralizing antibodies. It was hypothesized that live attenuated virus is launched in vivo, similarly our observation in vitro. However, live virus in mice was not detected in the viremia experiments. This suggests low viremia levels, which can represent a safety advantage for live vaccine. Previously, DNA-launched experimental vaccines were also prepared for Yellow fever virus, another member of the flavivirus family (Jiang et al., 2015; Tretyakova et al., 2014b), West Nile flavivirus (Hall et al., 2003; Yamshchikov, 2015; Yamshchikov et al., 2015), as well as vaccines for alphaviruses (Tretyakova et al., 2014a; Tretyakova et al., 2013). It was also shown by NGS that iDNA-derived Chikungunya virus (CHIKV) has higher genetic stability as compared to the cell culture-derived CHIKV virus (Hidajat et al., 2016). In addition, JEV infectious clone can serve as a vector platform to prepare chimeric JEV-based vaccines for other viruses including flaviviruses such as Zika, Dengue and West Nile viruses as was previously shown for chimeric Yellow fever-based vaccines (Guy et al., 2010). Finally, synthetic DNA for SA-14-14-2 JEV vaccine shows successful application of synthetic biology methods (Wimmer et al., 2009) for converting classic live attenuated vaccines into a DNA vaccine format. This, DNA vaccine can be configured not only for expression of subunit vaccines but also for expression of live vaccines (Pushko et al., 2016).

The subject matter described above is described by way of illustration only and should not be construed as limiting. Various modifications and changes may be made to the subject matter described herein without following the example embodiments and applications illustrated and described, and without departing from the true spirit and scope of the present invention, which is set forth in the following claims.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

REFERENCES

Bharati, K., Appaiahgari, M. B., Vrati, S., 2005. Effect of cytokine-encoding plasmid delivery on immune response to Japanese encephalitis virus DNA vaccine in mice. Microbio. Immunol. 49, 349-353.

CDC, 2016. Japanese Encephalitis Vaccine.

Guy, B., Guirakhoo, F., Barban, V., Higgs, S., Monath, T. P., Lang, J., 2010. Preclinical and clinical development of YFV 17D-based chimeric vaccines against Dengue, West Nile and Japanese encephalitis viruses. Vaccine 28, 632-649.

Hall, R. A., Nisbet, D. J., Pham, K. B., Pyke, A. T., Smith, G. A., Khromykh, A. A., 2003. DNA vaccine coding for the full-length infectious Kunjin virus RNA protects mice against the New York strain of West Nile virus. Proc Natl Acad Sci USA 100, 10460-10464.

Halstead, S. B., Thomas, S. J., 2011. New Japanese encephalitis vaccines: alternatives to production in mouse brain. Expert Rev Vaccines 10, 355-364.

Hidajat, R., Nickols, B., Forrester, N., Tretyakova, I., Weaver, S., Pushko, P., 2016. Next generation sequencing of DNA-launched Chikungunya vaccine virus. Virology 490, 83-90.

Jiang, X., Dalebout, T. J., Lukashevich, I. S., Bredenbeek, P. J., Franco, D., 2015. Molecular and immunological characterization of a DNA-launched Yellow fever virus 17D infectious clone. J. Gen. Virol. 96, 804-814.

Kaur, R., Sachdeva, G., Vrati, S., 2002. Plasmid DNA immunization against Japanese encephalitis virus: immunogenicity of membrane-anchored and secretory envelope protein. J. Infect. Dis. 185, 1-12.

Khromykh, A. A., Meka, H., Guyatt, K. J., Westaway, E. G., 2001. Essential role of cyclization sequences in flavivirus RNA replication. J. Virol. 75, 6719-6728.

Konishi, E., Ajiro, N., Nukuzuma, C., Mason, P. W., Kurane, I., 2003. Comparison of protective efficacies of plasmid DNAs encoding Japanese encephalitis virus proteins that induce neutralizing antibody or cytotoxic T lymphocytes in mice. Vaccine 21, 3675-3683.

Konishi, E., Yamaoka, M., Khin Sane, W., Kurane, I., Takada, K., Mason, P. W., 1999. The anamnestic neutralizing antibody response is critical for protection of mice from challenge following vaccination with a plasmid encoding the Japanese encephalitis virus premembrane and envelope genes. J. Virol. 73, 5527-5534.

Li, J., Gao, N., Fan, D., Chen, H., Sheng, Z., Fu, S., Liang, G., An, J., 2016. Cross-protection induced by Japanese encephalitis vaccines against different genotypes of Dengue viruses in mice. Sci Rep 6, 19953.

Lukashevich, P.P.P.P.B.I.S., 2014. Experimental DNA-launched live-attenuated vaccines against infections caused by Flavi- and alphaviruses, in: Igor S. Lukashevich, H. S. (Ed.), Novel Technologies for Vaccine Development. Springer Vienna.

Lutticken, D., Segers, R. P., Visser, N., 2007. Veterinary vaccines for public health and prevention of viral and bacterial zoonotic diseases. Rev Sci Tech 26, 165-177.

Messer, W. B., Yount, B., Hacker, K. E., Donaldson, E. F., Huynh, J. P., de Silva, A. M., Baric, R. S., 2012. Development and characterization of a reverse genetic system for studying Dengue virus serotype 3 strain variation and neutralization. PLoS neglected tropical diseases 6, e1486.

Mishin, V. P., Cominelli, F., Yamshchikov, V. F., 2001. A 'minimal' approach in design of flavivirus infectious DNA. Virus Res. 81, 113-123.

Onions, D., Cote, C., Love, B., Toms, B., Koduri, S., Armstrong, A., Chang, A., Kolman, J., 2011. Ensuring the safety of vaccine cell substrates by massively parallel sequencing of the transcriptome. Vaccine 29, 7117-7121.

Plotkin, S. A., 2010. Correlates of protection induced by vaccination. Clin Vaccine Immunol 17, 1055-1065.

Poirier, E. Z., Vignuzzi, M., 2017. Virus Population Dynamics During Infection. Current Opinion in Virology, 23:82-87.

Pushko, P., Geisbert, J., Parker, M., Jahrling, P., Smith, J., 2001. Individual and bivalent vaccines based on alphavirus replicons protect guinea pigs against infection with Lassa and Ebola viruses. J. Virol. 75, 11677-11685.

Pushko, P., Lukashevich, I. S., Weaver, S. C., Tretyakova, I., 2016. DNA-launched live-attenuated vaccines for biodefense applications. Expert Rev Vaccines 15, 1223-1234.

Putnak, R., Porter, K., Schmaljohn, C., 2003. DNA vaccines for flaviviruses. Adv. Virus Res. 61, 445-468.

Rice, C. M., Grakoui, A., Galler, R., Chambers, T. J., 1989. Transcription of infectious Yellow fever RNA from full-length cDNA templates produced by in vitro ligation. New Biol 1, 285-296.

Saito, Y., Moi, M. L., Takeshita, N., Lim, C. K., Shiba, H., Hosono, K., Saijo, M., Kurane, I., Takasaki, T., 2016. Japanese encephalitis vaccine-facilitated Dengue virus infection-enhancement antibody in adults. BMC Infect. Dis. 16, 578.

Shahmuradov, I A., Mohamad Razali R., Bougouffa S., Radovanovic A, Bajic V B, 2017, bTSSfinder a novel tool for the prediction of promoters in cyanobacteria and *Escherichia coli*. Bioinformatics 33(3):334-340.

Sheng, Z., Gao, N., Cui, X., Fan, D., Chen, H., Wu, N., Wei, J., An, J., 2016. Electroporation enhances protective immune response of a DNA vaccine against Japanese encephalitis in mice and pigs. Vaccine 34, 5751-5757.

Tretyakova, I., Hearn, J., Wang, E., Weaver, S., Pushko, P., 2014a. DNA vaccine initiates replication of live attenuated chikungunya virus in vitro and elicits protective immune response in mice. J. Infect. Dis. 209, 1882-1890.

Tretyakova, I., Lukashevich, I. S., Glass, P., Wang, E., Weaver, S., Pushko, P., 2013. Novel vaccine against Venezuelan equine encephalitis combines advantages of DNA immunization and a live attenuated vaccine. Vaccine 31, 1019-1025.

Tretyakova, I., Nickols, B., Hidajat, R., Jokinen, J., Lukashevich, I. S., Pushko, P., 2014b. Plasmid DNA initiates replication of Yellow fever vaccine in vitro and elicits virus-specific immune response in mice. Virology 468-470, 28-35.

Tsetsarkin, K. A., Kenney, H., Chen, R., Liu, G., Manukyan, H., Whitehead, S. S., Laassri, M., Chumakov, K., Pletnev, A. G., 2016. A Full-Length Infectious cDNA Clone of Zika Virus from the 2015 Epidemic in Brazil as a Genetic Platform for Studies of Virus-Host Interactions and Vaccine Development. MBio 7.

WHO, 2015. Japanese encephalitis. Fact sheet No 386.

Wimmer, E., Mueller, S., Tumpey, T. M., Taubenberger, J. K., 2009. Synthetic viruses: a new opportunity to understand and prevent viral disease. Nat. Biotechnol. 27, 1163-1172.

Wu, C. J., Li, T. L., Huang, H. W., Tao, M. H., Chan, Y. L., 2006. Development of an effective Japanese encephalitis virus-specific DNA vaccine. Microbes Infect 8, 2578-2586.

Wu, Y. C., Liu, S. T., 2010. A sequence that affects the copy number and stability of pSW200 and ColE1. J. Bacteriol. 192, 3654-3660.

Yamshchikov, V., 2015. Development of a human live attenuated West Nile infectious DNA vaccine: conceptual design of the vaccine candidate. Virology 484, 59-68.

Yamshchikov, V., Manuvakhova, M., Rodriguez, E., 2015. Development of a human live attenuated West Nile infectious DNA vaccine: Suitability of attenuating mutations found in SA14-14-2 for WN vaccine design. Virology 487, 198-206.

Yamshchikov, V., Mishin, V., Cominelli, F., 2001. A new strategy in design of +RNA virus infectious clones enabling their stable propagation in E. coli. Virology 281, 272-280.

Zhai, Y., Zhou, Y., Li, X., Feng, G., 2015. Immune-enhancing effect of nano-DNA vaccine encoding a gene of the prME protein of Japanese encephalitis virus and BALB/c mouse granulocyte-macrophage colony-stimulating factor. Mol Med Rep 12, 199-209.

The invention claimed is:

1. A vector comprising a DNA encoding a RNA molecule operably linked to a promoter suitable for expression of the DNA in a eukaryotic cell, wherein the RNA molecule encodes an infectious positive single stranded ((+)SS) RNA virus, wherein the (+)SS RNA virus is from the family Flaviviridae, wherein the DNA comprises three introns, and wherein the DNA encoding the RNA molecule comprises SEQ ID NO: 1;

the DNA encoding the RNA molecule comprises at least 80%, 85%, 90%, 95%, 96%, 97%, 98%, or 99% sequence identity with SEQ ID NO: 1, and the introns in SEQ ID NO: 1 are intact;

the DNA comprises at least 80%, 85%, 90%, 95%, 96%, 97%, 98%, or 99% sequence identity with a DNA encoding nucleic acid sequence of JEV SA14-14-2 strain and the introns are inserted immediately after nucleotide 414, nucleotide 2213, and nucleotide 3134 of the DNA encoding the nucleic acid sequence of JEV SA14-14-2 strain; or the DNA encodes nucleic acid sequence of JEV SA14-14-2 strain and the introns are inserted immediately after nucleotide 414, nucleotide 2213, and nucleotide 3134 of the DNA encoding the nucleic acid sequence of JEV SA14-14-2 strain.

2. The vector of claim 1, wherein the (+)SS RNA virus comprises a flavivirus.

3. The vector of claim 2, wherein the flavivirus is JEV.

4. A vector comprising a DNA encoding a chimeric RNA molecule of a chimeric infectious (+)SS RNA virus, wherein the DNA is operably linked to a promoter suitable for expression of the DNA in a eukaryotic cell, wherein the chimeric RNA molecule comprises nucleic acid sequences from at least two different (+)SS RNA viruses from the family Flaviviridae, wherein the DNA comprises three introns, and wherein
the DNA encoding the chimeric RNA molecule comprises nucleotides 1001 to 4477 of SEQ ID NO: 1; and
the DNA encoding the chimeric RNA comprises at least 80% or 85% of the entire nucleic acid sequence of JEV SA14-14-2 strain.

5. The vector of claim 4, wherein the (+)SS RNA virus is encoded by a chimeric RNA molecule comprising the RNA of at least two different flaviviruses.

6. The vector of claim 4, wherein the at least two different (+)SS RNA viruses comprise JEV and at least one of Dengue virus, Yellow fever virus, West Nile virus, tick borne encephalitis virus, Hepatitis C virus, or Zika virus.

7. The vector of claim 5, wherein the at least two different flaviviruses comprise JEV and at least one of Dengue virus, Yellow fever virus, West Nile virus, tick borne encephalitis virus, Hepatitis C virus, or Zika virus.

8. The vector of claim 7, wherein the at least two different flaviviruses are JEV and Zika virus.

9. The vector of claim 1, wherein at least one of the introns contain a stop codon or several stop codons.

10. The vector of claim 1, wherein the infectious (+)SS RNA virus is a nonpathogenic virus and/or an attenuated virus.

11. The vector of claim 1, wherein the infectious (+)SS RNA virus is a nonpathogenic and attenuated virus.

12. The vector of claim 1, wherein the promoter comprises a CMV promoter, a RSV promoter, a SV40 promoter, a HSV promoter, a human Pol I promoter, a human Pol II promoter, or a human Pol III promoter.

13. A pharmaceutical composition comprising the vector of claim 1 and a pharmaceutically acceptable carrier.

14. A pharmaceutical composition comprising the vector of claim 10 and a pharmaceutically acceptable carrier.

15. An immunogenic composition comprising an effective amount of a vector of claim 10.

16. An immunogenic composition comprising an effective amount of the vector of claim 1.

17. A method of preparing a homogeneous clonally purified live (+)SS RNA virus population, wherein the method comprises transfecting the vector of claim 1 into a eukaryotic cell and isolating (+)SS RNA viruses, thereby obtaining the homogeneous clonally purified live (+)SS RNA virus population.

18. The method of claim 17, wherein the eukaryotic cell is a Vero cell, a CHO cell, or a MDCK cell.

19. A method of preparing an immunogenic composition, wherein the method comprises transfecting the vector of claim 10 into a eukaryotic cell and isolating the (+)SS RNA viruses, thereby obtaining an immunogenic composition.

20. The method of claim 19, wherein the eukaryotic cell is a Vero cell, a CHO cell, or a MDCK cell.

21. A method of preparing a stable plasmid, wherein the method comprises a DNA encoding a genomic RNA of an infectious (+)SS RNA virus, wherein the (+)SS RNA virus is from the family Flaviviridae, wherein the method comprises introducing three introns into the DNA, and wherein
the DNA encoding the RNA molecule comprises SEQ ID NO: 1;
the DNA encoding the RNA molecule comprises at least 80%, 85%, 90%, 95%, 96%, 97%, 98%, or 99% sequence identity with SEQ ID NO: 1, and the introns in SEQ ID NO: 1 are intact;
the DNA comprises at least 80%, 85%, 90%, 95%, 96%, 97%, 98%, or 99% sequence identity with a DNA encoding nucleic acid sequence of JEV SA14-14-2 strain and the introns are inserted immediately after nucleotide 414, nucleotide 2213, and nucleotide 3134 of the DNA encoding the nucleic acid sequence of JEV SA14-14-2 strain; or
the DNA encodes nucleic acid sequence of JEV SA14-14-2 strain and the introns are inserted immediately after nucleotide 414, nucleotide 2213, and nucleotide 3134 of the DNA encoding the nucleic acid sequence of JEV SA14-14-2 strain.

22. A method of preparing a vector of claim 1, wherein the method comprises transfecting the vector of claim 1 into a host cell and isolating the vector from the host cell.

23. An isolated cell comprising the vector of claim 1.

24. The isolated cell of claim 23, wherein the cell comprises a prokaryotic cell or eukaryotic cell.

25. The cell of claim 24, wherein the prokaryotic cell comprises bacterial cells or wherein the eukaryotic cell comprises mammalian cells.

26. The method of claim 17, wherein transfecting the vector comprises transfecting the vector in vivo.

27. The method of claim 19, wherein transfecting the vector comprises transfecting the vector in vivo.

* * * * *

SEQUENCE LISTING

```
<160> NUMBER OF SEQ ID NOS: 1

<210> SEQ ID NO 1
<211> LENGTH: 14767
<212> TYPE: DNA
<213> ORGANISM: Artificial Sequence
<220> FEATURE:
<223> OTHER INFORMATION: pMG8009

<400> SEQUENCE: 1
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcaggcgcc       240
attcgccatt caggctgcgc aactgttggg aagggcgatc ggtgcgggcc tcttcgctat       300
tacgccagct ggcgaaaggg ggatgtgctg caaggcgatt aagttgggta acgccagggt       360
tttcccagtc acgacgttgt aaaacgacgg ccagtgaatt cggcgcgcct gacattgatt       420
attgactagt tattaatagt aatcaattac ggggtcatta gttcatagcc catatatgga       480
gttccgcgtt acataactta cggtaaatgg cccgcctggc tgaccgccca acgacccccg       540
cccattgacg tcaataatga cgtatgttcc catagtaacg ccaataggga ctttccattg       600
acgtcaatgg gtggagtatt tacggtaaac tgcccacttg gcagtacatc aagtgtatca       660
tatgccaagt acgccccta ttgacgtcaa tgacggtaaa tggcccgcct ggcattatgc       720
ccagtacatg accttatggg actttcctac ttggcagtac atctacgtat tagtcatcgc       780
tattaccatg gtgatgcggt tttggcagta catcaatggg cgtggatagc ggtttgactc       840
acggggattt ccaagtctcc accccattga cgtcaatggg agtttgtttt ggcaccaaaa       900
tcaacgggac tttccaaaat gtcgtaacaa ctccgcccca ttgacgcaaa tgggcggtag       960
gcgtgtacgg tgggaggtct atataagcag agctctctgg ctaactagag agaagtttat      1020
```

-continued

```
ctgtgtgaac ttcttggctt agtatcgtag agaagaatcg agagattagt gcagtttaaa   1080
cagttttta gaacggaaga taaccatgac taaaaaacca ggagggcccg gtaaaaaccg     1140
ggctatcaat atgctgaaac gcggcctacc ccgcgtattc ccactagtgg gagtgaagag    1200
ggtagtaatg agcttgttgg acggcagagg gccagtacgt ttcgtgctgg ctcttatcac    1260
gttcttcaag tttacagcat tagccccgac caaggcgctt tcaggccgat ggaaagcagt    1320
ggaaaagagt gtggcaatga acatcttac tagtttcaaa cgagaacttg gaacactcat     1380
tgacgccgtg aacaagcggg gcagaaagca aaacaaaaga ggaggtaagt atcaaggtta    1440
caagacaggt ttaaggagac caatagaaac tgggcttgtc gagacagaga agactcttgc    1500
gtttctgata ggcacctatt ggtcttactg acatccactt tgcctttctc tccacaggaa    1560
atgaaggctc aatcatgtgg ctcgcgagct tggcagttgt catagcttgt gcaggagcca    1620
tgaagttgtc gaatttccag gggaagcttt tgatgaccat caacaacacg gacattgcag    1680
acgttatcgt gattcccacc tcaaaaggag agaacagatg ctgggtccgg gcaatcgacg    1740
tcggctacat gtgtgaggac actatcacgt acgaatgtcc taagcttacc atgggcaatg    1800
atccagagga tgtggattgc tggtgtgaca accaagaagt ctacgtccaa tatggacggt    1860
gcacgcggac caggcattcc aagcgaagca ggagatccgt gtcggtccaa acacatgggg    1920
agagttcact agtgaataaa aaagaggctt ggctggattc aacgaaagcc acacgatatc    1980
tcatgaaaac tgagaactgg atcataagga atcctggcta tgctttcctg gcggcggtac    2040
ttggctggat gcttggcagt aacaacggtc aacgcgtggt atttaccatc ctcctgctgt    2100
tggtcgctcc ggcttacagt tttaattgtc tgggaatggg caatcgtgac ttcatagaag    2160
gagccagtgg agccacttgg gtggacttgg tgctagaagg agacagctgc ttgacaatca    2220
tggcaaacga caaaccaaca ttggacgtcc gcatgattaa catcgaagct agccaacttg    2280
ctgaggtcag aagttactgc tatcatgctt cagtcactga catctcgacg gtggctcggt    2340
gccccacgac tggagaagcc cacaacgaga agcgagctga tagtagctat gtgtgcaaac    2400
aaggcttcac tgaccgtggg tggggcaacg gatgtggatt tttcgggaag ggaagcattg    2460
acacatgtgc aaaattctcc tgcaccagta aagcgattgg gagaacaatc cagccagaaa    2520
acatcaaata caaagttggc atttttgtgc atggaaccac cacttcggaa aaccatggga    2580
attattcagc gcaagttggg gcgtcccagg cggcaaagtt tacagtaaca cccaatgctc    2640
cttcggtagc cctcaaactt ggtgactacg gagaagtcac actggactgt gagccaagga    2700
gtggactgaa cactgaagcg ttttacgtca tgaccgtggg gtcaaagtca tttctggtcc    2760
atagggagtg gtttcatgac ctcgctctcc cctggacgtc cccttcgagc acagcgtgga    2820
gaaacagaga actcctcatg gaatttgaag gggcgcacgc cacaaaacag tccgttgttg    2880
ctcttgggtc acaggaagga ggcctccatc atgcgttggc aggagccatc gtggtggagt    2940
actcaagctc agtgatgtta acatcaggcc acctgaaatg taggctgaaa atggacaaac    3000
tggctctgaa aggcacaacc tatggcatgt gtacagaaaa attctcgttc gcgaaaaatc    3060
cggtggacac tggtcacgga acagttgtca ttgaactctc ctactctggg agtgatggcc    3120
cctgcaaaat tccgattgtt tccgttgcga gcctcaatga catgaccccc gttgggcggc    3180
tggtgacagt gaaccccttc gtcgcgactt ccagtgccaa ctcaaaggtg ctggtcgaga    3240
tggaaccccc cttcggagac tcctacatcg tagttggaag gggagacaag cagatcaacc    3300
accattggca caaagctgga agcacgctgg gcaaggcctt tcaacaact tgaaggtaa      3360
ggggctcaca gtagcaggct tgaggtctgg acatatatat gggtgacaat gacatccact    3420
```

```
ttgcctttct ctccacaggg agctcaaaga ctggcagcgt tgggcgacac agcctgggac    3480
tttggctcta ttggaggggt cttcaactcc ataggaagag ccgttcacca agtgtttggt    3540
ggtgccttca gaacactctt tgggggaatg tcttggatca cacaagggct aatgggtgcc    3600
ctactgctct ggatgggcgt caacgcacga gaccgatcaa ttgctttggc cttcttagcc    3660
acaggaggtg tgctcgtgtt cttagcgacc aatgtgcatg ctgacactgg atgtgccatt    3720
gacatcacaa gaaagagat gagatgtgga agtggcatct tcgtgcacaa cgacgtggaa    3780
gcctgggtgg ataggtataa atatttgcca gaaacgccca gatccctagc gaagatcgtc    3840
cacaaagcgc acaaggaagg cgtgtgcgga gtcagatctg tcactagact ggagcaccaa    3900
atgtgggaag ccgtaaggga cgaattgaac gtcctgctca agagaatgc agtggacctc    3960
agtgtggttg tgaacaagcc cgtgggaaga tatcgctcag cccctaaacg cctatccatg    4020
acgcaagaga agtttgaaat gggctggaaa gcatgggaa aaagcatcct ctttgccccg    4080
gaattggcta actccacatt tgtcgtagat ggacctgaga caaggaatg ccctgatgag    4140
cacagagctt ggaacagcat gcaaatcgaa gacttcggct ttggcatcac atcaacccgt    4200
gtgtggctga aaattagaga ggagagcact gacgagtgtg atggagcgat cataggcacg    4260
gctgtcaaag acatgtggc agtccatagt gacttgtcgt actggattga gagtcgctac    4320
aacgacacat ggaaacttga gagggcagtc tttggagagg taagccagcc caggcctcgc    4380
cctccagctc aaggcgggac aggtgcccta gagtagcctg catccaggga caggcccag    4440
ccgggtgctg acacgtccac ctccatctct tcctcaggtc aaatcttgca cttggccaga    4500
gacacacacc ctttggggag atgatgttga ggaaagtgaa ctcatcattc cgcacaccat    4560
agccggacca aaaagcaagc acaatcggag ggaagggtat aagacacaaa accagggacc    4620
ttgggatgag aatggcatag tcttggactt tgattattgc ccagggacaa aagtcaccat    4680
tacagaggat tgtagcaaga gaggcccttc ggtcagaacc actactgaca gtggaaagtt    4740
gatcactgac tggtgctgtc gcagttgctc ccttccgccc ctacgattcc ggacagaaaa    4800
tggctgctgg tacggaatgg aaatcagacc tgttatgcat gatgaaacaa cactcgtcag    4860
atcacaggtt catgctttca aaggtgaaat ggttgaccct tttcagctgg gccttctggt    4920
gatgtttctg gccacccagg aagtccttcg caagaggtgg acggccagat tgaccattcc    4980
tgcggttttg ggggtcctac ttgtgctgat gcttgggggt atcacttaca ctgatttggc    5040
gaggtatgtg gtgctagtcg ctgctgcttt cgcagaggcc aacagtggag gagacgtcct    5100
gcaccttgct ttgattgctg tttttaagat ccaaccagca ttttagtga tgaacatgct    5160
tagcacgaga tggacgaacc aagaaaacgt ggttctggtc ctaggggctg cctttttcca    5220
attggcctca gtagatctgc aaataggagt ccacggaatc ctgaatgccg ccgctatagc    5280
atggatgatt gtccgagcga tcaccttccc cacaacctcc tccgtcacca tgccagtctt    5340
agcgcttcta actccgggga tgagggctct ataccctagac acttacagaa tcatcctcct    5400
cgtcataggg atttgctccc tgctgcacga gaggaaaaag accatggcga aaagaaagg    5460
agctgtactc ttgggcttag cgctcacatc cactggatgg ttctcgccca ccactatagc    5520
tgccggacta atggtctgca cccaaacaa gaagagaggg tggccagcta ctgagttttt    5580
gtcggcagtt ggattgatgt ttgccatcgt aggtggtttg gccgagttgg atattgaatc    5640
catgtcaata cccttcatgc tggcaggtct catggcagtg tcctacgtgg tgtcaggaaa    5700
agcaacagat atgtggcttg aacgggccgc cgacatcagc tgggatatgg gtgctgcaat    5760
```

```
cacaggaagc agtcggaggc tggatgtgaa actggatgat gacggagatt tcacttgat      5820
tgatgatccc ggtgttccat ggaaggtctg ggtcctgcgc atgtcttgca ttggcttagc     5880
cgccctcacg ccttgggcca tcgttcccgc cgctttcggt tattggctca ctttaaaaac    5940
aacaaaaaga gggggcgtgt tttgggacac gccatcccca aaaccttgct caaaaggaga    6000
caccactaca ggagtctacc gaattatggc tagagggatt cttggcactt accaggccgg    6060
cgtcggagtc atgtacgaga atgttttcca cacactatgg cacacaacta gaggagcagc    6120
cattgtgagt ggagaaggaa aattgacgcc atactggggt agtgtgaaag aagaccgcat    6180
agcttacgga ggcccatgga ggtttgaccg aaaatggaat ggaacagatg acgtgcaagt    6240
gatcgtggta gaaccgggga agggcgcagt aaacatccag acaaaaccag gagtgtttcg    6300
gactcccttc ggggaggttg gggctgttag tctggattac ccgcgaggaa catccggctc    6360
acccattctg gattccaatg gagacattat aggcctatac ggcaatggag ttgagcttgg    6420
cgatggctca tacgtcagcg ccatcgtgca gggtgaccgt caggaggaac cagtcccaga    6480
agcttacacc ccaaacatgt tgagaaagag acagatgact gtgctagatt tgcaccctgg    6540
ttcagggaaa accaggaaaa ttctgccaca ataattaag gacgctatcc agcagcgcct     6600
aagaacagct gtgttggcac cgacgcgggt ggtagcagca gaaatggcag aagctttgag    6660
agggctccca gtacgatatc aaacttcagc agtgcagaga gagcaccaag ggaatgaaat    6720
agtggatgtg atgtgccacg ccactctgac ccatagactg atgtcaccga acagagtgcc    6780
caactacaac ctatttgtca tggatgaagc tcatttcacc gacccagcca gtatagccgc    6840
acgaggatac attgctacca aggtggaatt aggggaggca gcagccatct ttatgacagc    6900
gaccccgcct ggaaccacgg atcctttcc tgactcaaat gccccaatcc atgatttgca    6960
agatgagata ccagacaggg catggagcag tggatacgaa tggatcacag aatatgcggg    7020
taaaaccgtg tggtttgtgg cgagcgtaaa aatggggaat gagattgcaa tgtgcctcca    7080
aagagcgggg aaaaaggtca tccaactcaa ccgcaagtcc tatgacacag ataccccaaa    7140
atgtaagaat ggagactggg attttgtcat taccaccgac atctctgaaa tgggggccaa    7200
cttcggtgcg agcagggtca tcgactgtag aaagagcgtg aaacccacca tcttagaaga    7260
gggagaaggc agagtcatcc tcggaaaccc atctcccata accagtgcaa gcgcagctca    7320
acggaggggc agagtaggca gaaaccccaa tcaagttgga gatgaatacc actatgggg    7380
ggctaccagt gaagatgaca gtaacctagc ccattggaca gaggcaaaga tcatgttaga    7440
caacatacac atgcccaatg gactggtggc ccagctctat ggaccagaga gggaaaaggc    7500
tttcacaatg gatggcgaat accgtctcag aggtgaagaa aagaaaaact tcttagagct    7560
gcttaggacg gctgacctcc cggtgtggct ggcctacaag gtggcgtcca tggcattca    7620
gtacaccgac agaaagtggt gttttgatgg gccgcgtacg aatgccatac tggaggacaa    7680
caccgaggta gagatagtca cccggatggg tgagaggaaa atcctcaagc cgagatggct    7740
tgatgcaaga gtttatgcag atcaccaggc cctcaagtgg ttcaaagact ttgcagcagg    7800
gaagagatca gccgttagct tcatagaggt gctcggtcgc atgcctgagc atttcatggg    7860
aaagacgcgg gaagctttag acaccatgta cttggttgca acggctgaga aggtgggaa    7920
agcacaccga atggctctcg aagagctgcc agatgcactg gaaaccatca cacttattgt    7980
cgccattact gtgatgacag gaggattctt cctactaatg atgcagcgaa agggtatagg    8040
gaagatgggt cttggagctc tagtgctcac actagcctacc ttcttcctgt gggcggcaga    8100
ggttcctgga accaaaatag cagggaccct gctgatcgcc ctgctgctga tggtggttct    8160
```

```
catcccagaa ccggaaaaac agaggtcaca gacagataac caactggcgg tgtttctcat   8220
ctgtgtcttg accgtggttg gagtggtggc agcaaacgag tacgggatgc tagaaaaaac   8280
caaagcggat ctcaagagca tgtttggcgg aaagacgcag gcatcaggac tgactggatt   8340
gccaagcatg gcactggacc tgcgtccagc cacagcctgg gcactgtatg gggggagcac   8400
agtcgtgcta accccctcttc tgaagcacct gatcacgtcg aatacgtca ccacatcgct   8460 agcttcaatt aactcacaag ctggctcatt attcgtcttg ccacgaggcg tgccttttac   8520
cgacctagac ttgactgttg gcctcgtctt ccttggctgt tggggtcaag tcaccctcac   8580
aacgtttctg acagccatgg ttctggcgac acttcactat gggtacatgc tccctggatg   8640
gcaagcagaa gcactcaggg ctgcccagag aaggacagcg gctggaataa tgaagaatgc   8700
cgttgttgac ggaatggtcg ccactgatgt gcctgaactg gaaaggacta ctcctctgat   8760
gcaaaagaaa gtcggacagg tgctcctcat aggggtaagc gtggcagcgt cctcgtcaa   8820 ccctaatgtc accactgtga gagaagcagg ggtgttggtg acggcggcta cgcttacttt   8880
gtgggacaat ggagccagtg ccgtttggaa ttccaccaca gccacgggac tctgccatgt   8940
catgcgaggt agctacctgg ctggaggctc cattgcttgg actctcatca agaacgctga   9000
taagccctcc ttgaaaaggg gaaggcctgg gggcaggacg ctaggggagc agtggaagga   9060
aaaactaaat gccatgagta gagaagagtt ttttaaatac cggagagagg ccataatcga   9120
ggtggaccgc actgaagcac gcagggccag acgtgaaaat aacatagtgg gaggacatcc   9180
ggtttcgcga ggctcagcaa aactccgttg gctcgtggag aaaggatttg tctcgccaat   9240
aggaaaagtc attgatctag ggtgtgggcg tggaggatgg agctactacg cagcaaccct   9300
gaagaaggtc caggaagtca gaggatacac gaaaggtggg gcgggacatg aagaaccgat   9360
gctcatgcag agctacggct ggaacctggt ctccctgaag agtggagtgg acgtgtttta   9420
caaaccttca gagcccagtg ataccctgtt ctgtgacata ggggaatcct ccccaagtcc   9480
agaagtagaa gaacaacgca cactacgcgt cctagagatg acatctgact ggttgcaccg   9540
aggacctaga gagttctgca ttaaagttct ctgcccttac atgcccaagg ttatagaaaa   9600
aatggaagtt ctgcagcgtc gcttcggagg tgggctagtg cgtctccccc tgtcccgaaa   9660
ctccaatcac gagatgtatt gggttagtgg agccgctggc aatgtggtgc acgctgtgaa   9720
catgaccagc caggtattac tggggcgaat ggatcgcaca gtgtggagag gccaaagta   9780 tgaggaagat gtcaacctag ggagcggaac aagagccgtg ggaaagggag aagtccatag   9840
caatcaggag aaaatcaaga agagaatcca gaagcttaaa gaagaattcg ccacaacgtg   9900
gcacaaagac cctgagcatc cataccgcac ttggacatac cacggaagct atgaagtgaa   9960
ggctactggc tcagccagct ctctcgtcaa cggagtggtg aagctcatga gcaaaccttg  10020
ggacgccatt gccaacgtca ccaccatggc catgactgac accaccccctt ttggacagca  10080 aagagttttc aaggagaaag ttgacacgaa ggctcctgag ccaccagctg agccaaggga  10140
agtgctcaac gagaccacca actggctgtg gcctacttg tcacgggaaa aaagacccccg  10200 cttgtgcacc aaggaagaat tcattaagaa agttaacagc aacgcggctc ttggagcagt  10260
gttcgctgaa cagaatcaat ggagcacggc gcgtgaggct gtggatgacc cgcggttttg  10320
ggagatggtt gatgaagaga gggaaaacca tctgcgagga gagtgtcaca catgtatcta  10380
caacatgatg ggaaaagag agaagaagcc tggagagttt ggaaaagcta aggaagcag   10440 ggccatttgg ttcatgtggc ttggagcacg gtatctagag tttgaagctt tggggttcct  10500
```

```
gaatgaagac cattggctga gccgagagaa ttcaggaggt ggagtggaag gctcaggcgt   10560
ccaaaagctg ggatacatcc tccgtgacat agcaggaaag caaggaggga aaatgtacgc   10620
tgatgatacc gccgggtggg acactagaat taccagaact gatttagaaa atgaagctaa   10680
ggtactggag ctcctagacg gtgaacaccg catgctcgcc cgagccataa ttgaactgac   10740
ttacaggcac aaagtggtca aggtcatgag acctgcagca aaggaaaga ccgtgatgga    10800 cgtgatatca agaagatc aaggggggag tggacaggtg gtcacttatg ctcttaacac     10860
tttcacgaac atcgctgtcc agctcgtcag gctgatggag gctgaggggg tcattggacc   10920
acaacacttg gaacatctac ctaggaaaaa caagatagct gtcaggacct ggctctttga   10980
gaatggagag gagagagtga ccaggatggc gatcagcgga gacgactgtg ccgtcaaacc   11040
gctggacgac agattcgcca cagccctcca cttcctcaac gcaatgtcaa aggtcagaaa   11100
agacatccag gaatggaagc cttcgcatgg ctggcacgat tggcagcaag ttcccttctg   11160
ttctaaccat tttcaggaga ttgtgatgaa agatggaagg agtatagttg tcccgtgcag   11220
aggacaggat gagctgatag gcagggctcg catctctcct ggagctggat ggaatgtgaa   11280
ggacacagct tgcctggcca aagcatatgc acagatgtgg ctactcctat acttccatcg   11340
cagggacttg cgtctcatgg caaatgcgat ttgctcagca gtgccagtag attgggtgcc   11400
cacaggcagg acatcctggt caatacactc gaaggagag tggatgacca cggaagacat    11460
gctgcaggtc tggaacagag tttggattga agaaaatgaa tggatgatgg acaagactcc   11520
aatcacaagc tggacagacg ttccgtatgt gggaaagcgc gaggacatct ggtgtggcag   11580
cctcatcgga acgcgatcca gagcaacctg ggctgagaac atctatgcgg cgataaacca   11640
ggttagagct gtcattggga aagaaaatta tgttgactac atgacctcac tcaggagata   11700
cgaagacgtc ttgatccagg aagacagggt catctagtgt gatttaaggt agaaaagtag   11760
actatgtaaa caatgtaaat gagaaaatgc atgcatatgg agtcaggcca gcaaaagctg   11820
ccaccggata ctgggtagac ggtgctgcct gcgtctcagt cccaggagga ctgggttaac   11880
aaatctgaca acagaaagtg agaaagccct cagaaccgtc tcggaagtag gtccctgctc   11940
actggaagtt gaaagaccaa cgtcaggcca caaatttgtg ccactccgct agggagtgcg   12000
gcctgcgcag ccccaggagg actgggttac caaagccgtt gaggccccca cggcccaagc   12060
ctcgtctagg atgcaataga cgaggtgtaa ggactagagg ttagaggaga ccccgtggaa   12120
acaacaacat gcggcccaag ccccctcgaa gctgtagagg aggtggaagg actagaggtt   12180
agaggagacc ccgcatttgc atcaaacagc atattgacac ctgggaatag actgggagat   12240
cttctgctct atctcaacat cagctactag gcacagagcg ccgaagtatg tagctggtgg   12300
tgaggaagaa cacaggatct ctcgagtggg tcggcatggc atctccacct cctcgcggtc   12360
cgacctgggc atccgaagga ggacgcacgt ccactcggat ggctaaggga gagccacgag   12420
ctcctcgaca gatcataatc agccatacca catttgtaga ggttttactt gctttaaaaa   12480
acctcccaca cctcccccctg aacctgaaac ataaaatgaa tgcaattgtt gttgttaact   12540
tgtttattgc agcttataat ggttacaaat aaagcaatag catcacaaat ttcacaaata   12600
aagcattttt ttcactgcat tctagttgtg gtttgtccaa actcatcaag atgtatacaa   12660
gcttggtgta atcatggtca tagctgtttc ctgtgtgaaa ttgttatccg ctcacaattc   12720
cacacaacat acgagccgga agcataaagt gtaaagcctg gggtgcctaa tgagtgagct   12780
aactcacatt aattgcgttg cgctcactgc ccgctttcca gtcgggaaac ctgtcgtgcc   12840
agctgcatta atgaatcggc caacgcgcgg ggagaggcgg tttgcgtatt gggcgctctt   12900
```

-continued

```
ccgcttcctc gctcactgac tcgctgcgct cggtcgttcg gctgcggcga gcggtatcag    12960
ctcactcaaa ggcggtaata cggttatcca cagaatcagg ggataacgca ggaaagaaca    13020
tgtgagcaaa aggccagcaa aaggccagga accgtaaaaa ggccgcgttg ctggcgtttt    13080
tccataggct ccgcccccct gacgagcatc acaaaaatcg acgctcaagt cagaggtggc    13140
gaaacccgac aggactataa agataccagg cgtttccccc tggaagctcc ctcgtgcgct    13200
ctcctgttcc gaccctgccg cttaccggat acctgtccgc ctttctccct tcgggaagcg    13260
tggcgctttc tcatagctca cgctgtaggt atctcagttc ggtgtaggtc gttcgctcca    13320
agctgggctg tgtgcacgaa ccccccgttc agcccgaccg ctgcgcctta tccggtaact    13380
atcgtcttga gtccaacccg gtaagacacg acttatcgcc actggcagca gccactggta    13440
acaggattag cagagcgagg tatgtaggcg gtgctacaga gttcttgaag tggtggccta    13500
actacggcta cactagaaga acagtatttg gtatctgcgc tctgctgaag ccagttacct    13560
tcggaaaaag agttggtagc tcttgatccg gcaaacaaac caccgctggt agcggtggtt    13620 ttttttgtttg caagcagcag attacgcgca gaaaaaaagg atctcaagaa gatcctttga    13680
tcttttctac ggggtctgac gctcagtgga acgaaaactc acgttaaggg attttggtca    13740
tgagattatc aaaaaggatc ttcacctaga tccttttaaa ttaaaaatga gttttaaat     13800 caagcccaat ctgaataatg ttacaaccaa ttaaccaatt ctgattagaa aaactcatcg    13860
agcatcaaat gaaactgcaa tttattcata tcaggattat caataccata tttttgaaaa    13920
agccgtttct gtaatgaagg agaaaactca ccgaggcagt tccataggat ggcaagatcc    13980
tggtatcggt ctgcgattcc gactcgtcca acatcaatac aacctattaa tttcccctcg    14040
tcaaaaataa ggttatcaag tgagaaatca ccatgagtga cgactgaatc cggtgagaat    14100
ggcaaaagtt tatgcatttc tttccagact tgttcaacag gccagccatt acgctcgtca    14160
tcaaaatcac tcgcatcaac caaaccgtta ttcattcgtg attgcgcctg agcgagacga    14220
aatacgcgat cgctgttaaa aggacaatta caaacaggaa tcgaatgcaa ccggcgcagg    14280
aacactgcca gcgcatcaac aatatttcac cctgaatcag gatattcttc taatacctgg    14340
aatgctgttt ttccggggat cgcagtggtg agtaaccatg catcatcagg agtacggata    14400
aaatgcttga tggtcggaag aggcataaat tccgtcagcc agtttagtct gaccatctca    14460
tctgtaacat cattggcaac gctacctttg ccatgtttca gaaacaactc tggcgcatcg    14520
ggcttcccat acaagcgata gattgtcgca cctgattgcc cgacattatc gcgagcccat    14580
ttatacccat ataaatcagc atccatgttg gaatttaatc gcggcctcga cgtttcccgt    14640
tgaatatggc tcataacacc ccttgtatta ctgtttatgt aagcagacag ttttattgtt    14700
catgatgata ttttttatc ttgtgcaatg taacatcaga gattttgaga cacgggccag    14760
agctgca                                                            14767
```